US012643878B2

(12) United States Patent
Baati et al.

(10) Patent No.: US 12,643,878 B2
(45) Date of Patent: Jun. 2, 2026

(54) DIAZINOXIMES SCAFFOLDS

(71) Applicants: CENTRE NATIONAL DE LA RECHERCHE SCIENTIFIQUE, Paris (FR); UNIVERSITÉ DE STRASBOURG, Strasbourg (FR); ETAT FRANÇAIS, SERVICE DE SANTÉ DES ARMÉES REPRÉSENTÉ PAR LE DÉLÉGUÉ GÉNÉRAL DE L'ARMEMENT, Paris (FR)

(72) Inventors: Rachid Baati, Strasbourg Cedex (FR); Mallikarjuna Reddy Nimmakayala, Strasbourg Cedex (FR); José Dias, Brétigny sur Orge (FR); Florian Nachon, Brétigny sur Orge (FR); Camille Voros, Strasbourg (FR); Raymond Franck Razafindrainibe, Schiltigheim (FR)

(73) Assignees: CENTRE NATIONAL DE LA RECHERCHE SCIENTIFIQUE, Paris (FR); UNIVERSITÉ DE STRASBOURG, Strasbourg (FR); ETAT FRANÇAIS SERVICE SE SANTÉ DES ARMÉES REPRÉSENTÉ PAR LE DÉLÉGUÉ GÉNTÉRAL DE L'ARMEMENT, Paris (FR)

( * ) Notice: Subject to any disclaimer, the term of this patent is extended or adjusted under 35 U.S.C. 154(b) by 529 days.

(21) Appl. No.: 18/043,646

(22) PCT Filed: Sep. 10, 2021

(86) PCT No.: PCT/EP2021/074985
§ 371 (c)(1),
(2) Date: Mar. 1, 2023

(87) PCT Pub. No.: WO2022/053641
PCT Pub. Date: Mar. 17, 2022

(65) Prior Publication Data

US 2023/0278980 A1 Sep. 7, 2023

(30) Foreign Application Priority Data

Sep. 11, 2020 (EP) .................................... 20306011

(51) Int. Cl.
*C07D 401/06* (2006.01)
*C07D 403/06* (2006.01)

(52) U.S. Cl.
CPC ......... *C07D 401/06* (2013.01); *C07D 403/06* (2013.01)

(58) Field of Classification Search
CPC .................................................... C07D 401/06
See application file for complete search history.

(56) References Cited

U.S. PATENT DOCUMENTS 5,238,941 A 8/1993 Stanek et al.

FOREIGN PATENT DOCUMENTS

| | | |
|---|---|---|
| DE | 33 28 808 A1 | 2/1985 |
| EP | 2 873 663 A1 | 5/2015 |
| EP | 3 696 170 A1 | 8/2020 |

(Continued)

OTHER PUBLICATIONS

Arnold et al: "Synthesis of Quaternary Pyrimidine bases, Potential Cholinesterase Reactivators", Chemischer Informationsdienst, Jan. 1, 1978, retrieved from the internet: http://www.wuebalib.com/cloud/literature-5f57AYdDy0QJ/html.

(Continued)

*Primary Examiner* — Golam M Shameem
(74) *Attorney, Agent, or Firm* — WCF IP

(57) ABSTRACT

The present invention relates to a compound of formulas (II) to (V). It also relates to a pharmaceutical composition comprising at least one compound of formulas (II) to (V) and at least one pharmaceutically acceptable support. Finally, it relates to the use of such a compound as a medicine, preferably in the treatment of a nervous and/or respiratory failure due to intoxication with at least one organophosphorus nerve agent by reactivation of hAChE; in the treatment of neurological diseases such as Alzheimer's disease; and/or in the treatment of cancer.

(II)

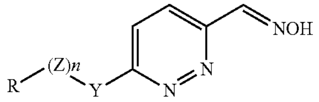

(III)

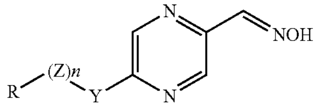

(IV)

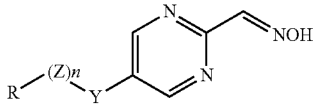

(V)

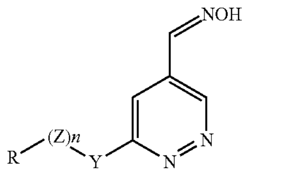

18 Claims, No Drawings

(56) References Cited

FOREIGN PATENT DOCUMENTS

| | | | |
|---|---|---|---|
| WO | 2005/094822 | A1 | 10/2005 |
| WO | 2019/084476 | A1 | 5/2019 |

OTHER PUBLICATIONS

Chandar et al: "Quantum chemical and steered molecular dynamics studies for one pot solution to reactivate aged acetylcholinesterase with alkylator oxime", Chemico-Biological Interactions, vol. 223, p. 58-68, Nov. 1, 2014.

Huo et al: "Iodine-mediated electrophilic cyclization of 2-alkynylbenzaldoximes leading to the formation of Iodoisoquinoline N-oxides", Tetrahedron Letters, vol. 49, No. 28, p. 5531-5533, Sep. 15, 2008.

Numata et al: "General synthetic method 1 for naphthyridines and their N-oxides containing isoquinolinic nitrogen", Synthesis, No. 2, p. 306-311, Jan. 1, 1999.

Pavlyuchenko et al: "2-CYANO-50[b-(trans-4-ALKYLCYCLOHEXYL)ETHYL]PYRIDINES", Journal of Organic Chemistry USSR, p. 967-971, 1986.

Su et al: "Studies on antidotes against organophosphorus poisoning-reactivation of inhibited cholinesterase. VI. Synthesis of 2-w-bromoalkylpyridinealdoxime and their derivatives", Shanghai Diyi Yixueyuan Xuebao, vol. 8, No. 1, p. 38-44, 1981.

Katz et al., ChemBioChem. 2015, 16, 2205-2215.

De Koning et al., Eur. J. Med. Chem. 2018, 157, 151-160.

Cadieux et al., Chemico-Biological Interactions 2016, 259, 133-141.

Carletti, E. et al. 2008.

Kitz, R.J., et al. 1965.

Worek, F., et al., 2004.

R. Cecchelli, S. Aday, E. Sevin, C. Almeida, M. Culot, L. Dehouck, C. Coisne, B. Engelhardt, M. P. Dehouck, L. Ferreira, PLoSOne 2014, 9.

C. Pedroso, A. Tellechea, L. Moura, I. Fidalgo-Carvalho, J. Duarte, E. Carvalho, L. Ferreira, PLoS One 2011 , 6.

DIAZINOXIMES SCAFFOLDS

The present invention relates to novel compounds having a diazinoxime scaffold. Such compounds may be useful for many therapeutic and non-therapeutic applications. The invention also relates to compositions, notably pharmaceutical compositions, comprising said compounds, and their use.

Organophosphorous nerve agents (OPNA) are extremely toxic compounds that comprise chemical warfare agents (CWA) including sarin, soman, cyclosarin, tabun, methylphosphonothioate (VX) and pesticides such as paraoxon, parathion and tetraethyl pyrophosphate (TEPP). Their acute toxicity results from the irreversible inhibition of acetylcholinesterase (AChE) through phosphylation of its catalytic serine, which results in the inability of the enzyme to hydrolyze acetylcholine (ACh). Accumulation of this neurotransmitter at cholinergic synapses occurs, leading to a permanent saturation of the muscarinic and nicotinic receptors which ultimately results in seizure and respiratory arrest. Depending on the class of OPNA and on the administrated dose, death can occur within a few minutes.

Due to the similarity between the chemical precursors of CWA and pesticides, and to the relatively simple chemistry involved in their synthesis, efforts to control the proliferation of these agents have proved of limited success. Therefore, the development of effective measures to counteract OPNA poisoning remains a challenging issue to protect and treat both civilian and military populations. The current treatment for OPNA poisoning consists in the administration of a combination of atropine (antimuscarinic agent) and diazepam (anticonvulsant drug), to limit convulsions, and of a standard pyridinium oxime (pralidoxime, trimedoxime, HI-6, obidoxime, or HLö-7) to reactivate AChE. Oximes exert their action on OPNA-inhibited AChE by attacking the phosphorous atom of the phosphylated serine, leading to the removal of the phosphonate and restoration of the enzyme's catalytic activity. However, it has been demonstrated that the current therapy results in unequal efficiency, and none of these oximes offer broad efficacy across the different OPNAs. Further limitations of oxime-based therapy include inability to cross the blood-brain barrier (BBB), inability to reactivate the "aged" enzyme, and rapid clearance from the circulation when tested in vivo. Animal model studies and recent clinical trials using pesticide poisoned individuals have shown uneven clinical benefits of these oximes, and even harm, so their true efficacy as antidotes has been debated at the World Health Organisation.

To overcome the disadvantages of the current medication, the development of new broad spectrum and bioavailable centrally active drugs is of crucial importance.

Over the past decades, there has been a growing interest in the development of non-ionic oximes reactivators of OPNA-inhibited hAChE (human AChE) to increase BBB permeability. For example, uncharged hybrid reactivators bearing 3-hydroxy-2-pyridinaldoxime as nucleophilic moiety and a peripheral site AChE ligand, exhibited increased affinity for the phosphylated enzyme, a large spectrum of reactivation and the ability to cross efficiently the BBB in vitro. Beside these discoveries, others heterocyclic, aromatic and acyclic nucleophilic oximes, as well as uncharged acetamido bis-oximes have been developed as antidotes, with more or less success in the reactivation of OPNA-inhibited AChE.

Recently, unusual non-oxime non-ionic new functional groups such as Mannich phenols that are capable of reactivating OPNA-inhibited AChE have been reported by Katz, Cadieux and De Koning (Katz et al, *ChemBioChem.* 2015, 16, 2205-2215; de Koning et al, *Eur. J. Med. Chem.* 2018, 157, 151-160; Cadieux et al, *Chemico-Biological Interactions* 2016, 259, 133-141). However, the mechanism of the reactivation is still unclear, and the development of these molecules is hampered by their low stability in biological media.

Recent findings have demonstrated the ability of a zwitterionic, centrally acting, brain penetrating oxime to reverse severe symptoms and rapidly reactivate sarin- and paraoxon inhibited AChE in vivo.

It is further obvious that the above-mentioned compounds are accessed only after tedious, non-flexible and lengthy multistep chemical synthesis due to their increased structural complexity.

Despite these innovative strategies for the development of reactivators, efforts towards shorter and more convergent synthetic routes to innovative broad spectrum and centrally effective antidotes are still needed. There is thus a remaining need for chemical compounds efficient in therapeutic applications, particularly against OPNA intoxications, with a broad spectrum and centrally effective. These compounds have to be quick and easy to synthetize.

Surprisingly, the inventors have now discovered that specific compounds, having a diazinoxime scaffold, fulfill these needs.

Indeed, such compounds are quick and very easy to produce thanks to a late-stage Sonogashira cross-coupling reaction, which leads to a short and expedient synthesis, without using protecting groups for the sensitive oximes. The compounds present very interesting properties: they have a low molecular weight, and exhibit a quite simple molecular structural design and a broad spectrum of reactivation of OPNA-inhibited AChE, especially with increased efficacy for VX and paraoxon, and a good potency against sarin.

Notably, these compounds may be used as antidotes against OPNA intoxications or as detoxifying or decontamination agents against organophosphorus compounds, or as sensors for OPNA detection, thanks to their effective and fast reactivation of hAChE without denaturing the same. They may also be used in the treatment of neurodegenerative diseases such as Alzheimer's disease. Finally, particularly the oxime compounds of the invention may be used as histone deacetylases (HDAC) inhibitors; consequently, they may be used in the treatment of cancer.

Thus, a first object of the present invention is a compound of formula (I):

(I)

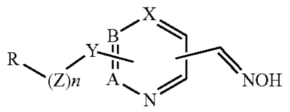

wherein the different groups are as defined in the detailed description below.

Another object of the present invention is a process for preparing the compounds of formula (I), especially by a Sonogashira reaction, as detailed below.

Another object of the present invention is a pharmaceutical composition comprising at least one compound of formula (I) and at least one pharmaceutically acceptable support.

Another object of the invention is a compound according to the invention, for use as a medicine.

A further object of the invention is a compound according to the invention for use in the treatment of a nervous and/or respiratory failure due to intoxication with at least one organophosphorous nerve agent.

Still a further object of this invention is a compound according to the invention for use in the treatment of neurological diseases such as Alzheimer's disease.

Still a further object of this invention is a compound according to the invention for use in the treatment of cancer.

A first object of the present invention is a compound of formula (I), or one of its pharmaceutically acceptable salts:

(I)

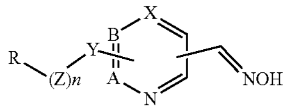

wherein:

A is a carbon atom (C), —CH— or a nitrogen atom (N);
B is a carbon atom (C), —CH— or a nitrogen atom (N);
X is a carbon atom (C), —CH— or a nitrogen atom (N);
Y is $—CH_2—CH_2—$, —C≡C— or —CH═CH—;
Z is $—CH_2—$,
n is an integer from 0 to 3; and
R is an alkyl group, a heteroalkyl, an aryl, a heteroaryl, a heterocycloalkyl, a biomolecule, a carboxyl group, a hydroxyl group, a cyano, an oxime, an hydroxamic group, a ketone, a thiol or thioether or thioester group, a phosphate, a phosphonate, phosphinate, phosphonium, sulfone, sulfonium, sulfate group, a fluorescent probe, or a group —N(R1)(R2), wherein R1 and R2 are each independently H, an alkyl group, an aryl or a heteroaryl.

As the carbon atom is tetravalent, each one of the carbon atoms for A, B and X may be linked to a hydrogen atom. Thus, in order words, A, B and X are each independently chosen from is C, —CH— or N.

When A is N and B═X═C or —CH—, then formula (I) is a pyridazine scaffold.

When A is C or —CH—, B is N and X═C or —CH—, then formula (I) is a pyrimidine scaffold.

When A=B═C or —CH—, and X is N, then formula (I) is a pyrazine scaffold.

By "pharmaceutically acceptable salt", it is meant any salt of a compound of formula (I) with an acid or a base. Preferably, the pharmaceutically acceptable salt is a chlorhydrate salt (also called hydrochloride). Such a salt may be obtained by using HCl. More preferably, the heteroaryl group of R comprises a nitrogen atom, which is complexed with HCl.

Preferably, the compound of the invention is a salt of a compound of formula (I), more preferably a chlorhydrate salt of a compound of formula (I).

The compound of formula (I) may be labeled with one or more isotopes such as $^{15}N$, $^{18}O$, $^{2}H$ or $^{3}H$. Preferably the compound is labeled on the ═N—OH group, with $^{15}N$. Indeed, such a stable, non-toxic and non-radioactive isotope would allow in vivo and in vitro biological studies and profiling.

By "alkyl", it is meant a linear hydrocarbon group preferably comprising from 1 to 20 carbon atoms, in particular from 1 to 15 carbon atoms, or a branched or cyclic hydrocarbon group comprising from 3 to 20 carbon atoms. Examples of alkyl groups include methyl, ethyl, n-propyl, isopropyl, n-butyl, isobutyl, tert-butyl, n-pentyl, isopentyl, n-hexyl, n-tridecyl, cyclohexyl and cyclohexylmethyl groups, and preferably ethyl, propyl, n-hexyl, n-tridecyl, cyclohexyl or cyclohexylmethyl group.

By "heteroalkyl", it is meant a heteroatom that is linked to any alkyl group. The heteroatom may be nitrogen, oxygen, sulfur, phosphorous or boron. A preferred heteroalkyl group is an alkoxy group. By "alkoxy", it is meant an oxygen linked to any alkyl group (—O-alkyl).

By "aryl", it is meant a monocyclic or polycyclic aromatic hydrocarbon group, which may be optionally substituted. Preferably, the aryl group is a phenyl, or a polycyclic aromatic hydrocarbon (PAH). A preferred PAH is pyrene. The aryl is preferably not substituted.

By "heteroaryl", it is meant an aryl group in which at least one carbon atom of the aromatic ring is substituted by a heteroatom, and which may be optionally substituted. The heteroatom may be nitrogen, oxygen, phosphorus or sulfur. Preferably the heteroatom is nitrogen. Examples of heteroaryl groups include pyridine, pyrrole, thiophene, furane, pyrimidine, pyrazine, pyridazine, triazole, tetrazine, triazine, imidazole, quinoline, thiazole, oxazole, tetrazole, oxadiazole, thiadiazole, pyrazole, imidazole, triazole, and isoxazole groups. Preferably, the heteroaryl group is a pyridine group such as 2-, 3- or 4-pyridino, more preferably a 3-pyridino. The heteroaryl is preferably not substituted. Alternatively, the heteroaryl is preferably an imidazole, preferably substituted by at least one alkyl group such as methyl.

A "heterocycloalkyl" refers to a non-aromatic saturated monocyclic or polycyclic ring comprising carbon and hydrogen atoms, in which at least one carbon atom of the ring is substituted by a heteroatom. The heteroatom may be nitrogen, oxygen, or sulfur. Preferably, the heterocycloalkyl group is a monocyclic ring comprising from 3 to 6, preferably from 4 to 6 carbon atoms. Preferably, the heterocycloalkyl group is an epoxide, morpholino, pyrazolidine, oxathiolane, tetrahydrofuran, dioxolane, piperidine, piperazine, thiomorpholine, tetrahydropyrane, oxetane or azetidine, such as 4-tetrahydropyrano or 3-oxetano or 3-azetidino. The heterocycloalkyl may be substituted or not.

By "biomolecule", it is meant a sugar moiety, a peptide moiety, an antibody, a virus, a DNA, a RNA or a protein moiety. The sugar moiety may be for example a glucose, fructose or sucrose moiety. A peptide moiety is a moiety typically comprising 1 to 50 amino acids. A protein moiety is a moiety typically comprising at least 51 amino acids, preferably from 60 to 500 amino acids.

By "fluorescent probe", it is meant a chemical function or a fluorophore endowed with fluorescent properties. The fluorescent moiety may be for example a fluoresceine, boron dipyrromethene (BODIPY), a coumarine, a cyanine, an Alexa Fluor, an acridine, a fluorone, a squaraine, a phenanthridine, a cyanine, an oxazine, a perylene, an anthracene or rhodamine moiety.

By "carboxyl group", it is meant a —COOH group.

By "cyano", it is meant a —CN group.

By "oxime", it is meant a —C(R')═N—OH group, wherein R' is H, an alkyl group or an amine group —NR3R4, wherein R3 and R4 are each H or an alkyl group. When R' is —NR3R4, then the oxime is an amidoxime group.

By "hydroxamic group", it is meant a R5-C(O)—N(OH)— or —C(O)—N(OH)—R5 group, wherein R5 is H or an alkyl group.

By "ketone", it is meant a group comprising the moiety —CO—. Preferably, the ketone is an alkyl group comprising the moiety —CO—.

By "thiol, thioether or thioester group", it is respectively meant a group comprising a moiety —SR6, wherein R6 is respectively H, alkyl or —CO—R7, wherein R7 is an alkyl group.

By hydroxyl group, it is meant a group —OH.

By "phosphonate", it is meant a group $—P(O)(OR8)_2$, wherein R8 are identical or different and are either H or an alkyl group. When both R8 are H, then the group is a phosphate, i.e. a group $—P(O)(OH)_2$.

By "phosphinate", it is meant a group —P(O)(OR9), wherein R9 is H or an alkyl group.

By "phosphonium", it is meant a cation $P(R10)_4^+$, wherein each R10 (identical or different) is an alkyl group.

By "sulfone", it is meant a group comprising a radical —SO2. Preferably, the sulfone is an alkyl group comprising a radical —SO2.

By "sulfonium", it is meant a cation $S(R11)_3^+$, wherein each R11 (identical or different) is an alkyl group.

By "sulfate group", it is meant —SO4.

Preferably, the —Y—(Z)n-R group is in position 6 or 5, and/or the oxime group is in position 3 or 2.

Preferably, R is a heteroaryl. Preferably, the heteroaryl group is a pyridine group such as 2-, 3- or 4-pyridino, preferably 3-pyridino. Preferably, the heteroaryl group is not substituted.

According to a first embodiment, A is N, B is C, X is —CH—, and the —Y—(Z)n-R group is in position 6; formula (I) is a pyridazine scaffold.

Preferably, the oxime group is in position 3, and the compound of the invention is a 6-substituted-3-pyridazinoxime of formula (II), or one of its pharmaceutically acceptable salts:

(II)

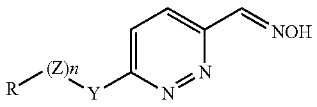

According to a second embodiment, A is C, B is —CH—, X is N, and the —Y—(Z)n-R group is in position 6; formula (I) is a pyrazine scaffold.

Preferably, the oxime group is in position 3, and the compound of the invention is a 6-substituted-3-pyrazinoxime of formula (III), or one of its pharmaceutically acceptable salts:

(III)

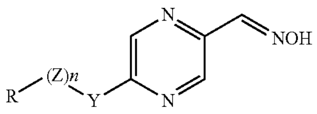

According to a third embodiment, A is C, B is N, X is —CH—, and the —Y—(Z)n-R group is in position 5; formula (I) is a pyrimidine scaffold.

Preferably, the oxime group is in position 2, and the compound of the invention is a 5-substituted-2-pyrimidinoxime of formula (IV), or one of its pharmaceutically acceptable salts:

(IV)

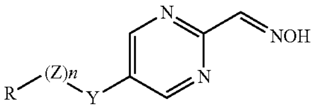

According to a fourth embodiment, A is N, B is C, X is —CH—, and the —Y—(Z)n-R group is in position 6; formula (I) is a pyridazine scaffold.

Preferably, the oxime group is in position 4, and the compound of the invention is a 6-substituted-4-pyridazinoxime of formula (V), or one of its pharmaceutically acceptable salts:

(V)

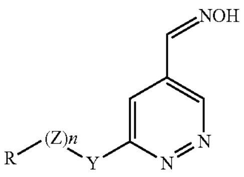

According to said first embodiment, it is preferred that the compound of formula (I) is a 6-substituted-3-pyridazinoxime of formula (II), or one of its pharmaceutically acceptable salts:

(II)

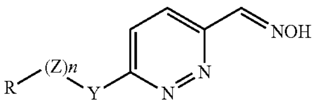

Preferably, Y is $—CH_2—CH_2—$ or —C≡C—, and n is 0, 1 or 2, preferably n is 0 or 2.

Preferably, R is a heteroaryl. Preferably said heteroaryl is not substituted. Preferably, said heteroaryl is a pyridine group such as 2-, 3- or 4-pyridino, preferably 3-pyridino. Alternatively, said heteroaryl is an imidazole, preferably substituted by at least an alkyl group such as methyl.

Preferably, according to said first embodiment, the compounds of formula (II) and their salts are such that:

A is N,

B is C,

X is —CH—,

Y is $—CH_2—CH_2—$ or —C≡C—, n is 0, 1 or 2, preferably n is 0 or 2; and

R is a heteroaryl, preferably said heteroaryl is not substituted and is a pyridine group such as 2-, 3- or 4-pyridino, preferably 3-pyridino, or said heteroaryl is an imidazole, preferably substituted by at least an alkyl group such as methyl.

Preferably, the compound of formula (II) or one of its pharmaceutically acceptable salts is chosen from the following compounds:

(E)-6-(pyridin-3-ylethynyl)pyridazine-3-carbaldehyde oxime 4:

4

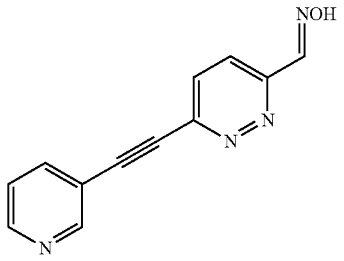

(E)-6-(pyridin-3-ylethynyl)pyridazine-3-carbaldehyde oxime hydrochloride NM-45:

NM-45

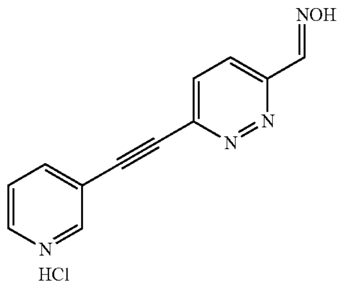

(E)-6-(2-(pyridin-3-yl)ethyl)pyridazine-3-carbaldehyde oxime 5:

5

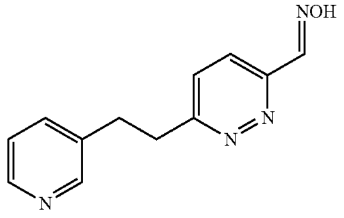

(E)-6-(2-(pyridin-3-yl)ethyl)pyridazine-3-carbaldehyde oxime hydrochloride NM-65:

NM-65

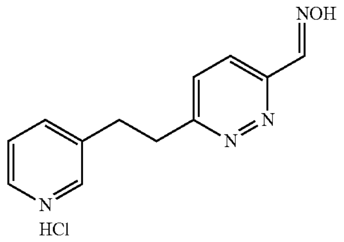

(E/Z)-6-(4-(pyridin-3-yl)but-1-ynyl)pyridazine-3-carbaldehyde oxime 7:

7

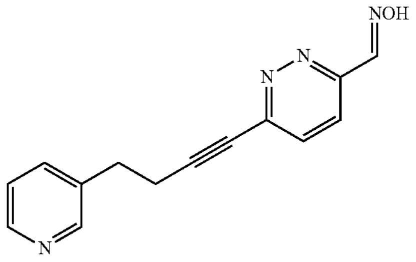

(E/Z)-6-(4-(pyridin-3-yl)but-1-ynyl)pyridazine-3-carbaldehyde oxime hydrochloride NM-184:

NM-184

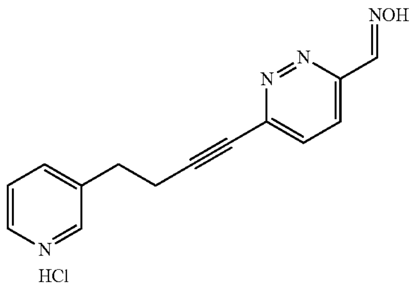

(E/Z)-6-(4-(pyridin-3-yl)butyl)pyridazine-3-carbaldehyde oxime 8:

8

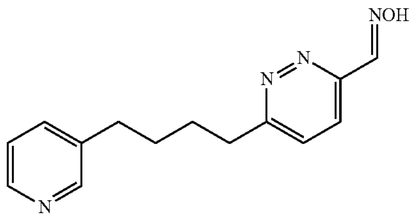

(E/Z)-6-(4-(pyridin-3-yl)butyl)pyridazine-3-carbaldehyde hydrochloride NM-201:

NM-201

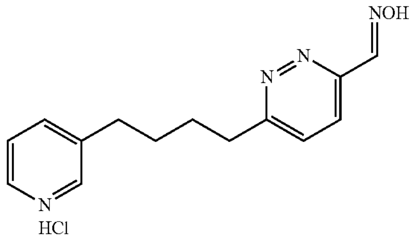

and (Z/E)-6-((1-methyl-1H-imidazol-5-yl)ethynyl)pyridazine-3-carbaldehyde oxime FR-156:

FR-156

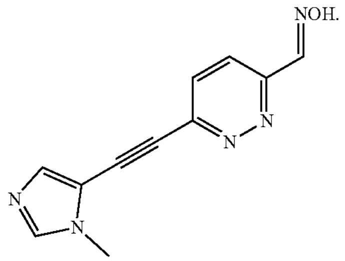

According to said second embodiment, it is preferred that the compound of the invention is a 6-substituted-3-pyrazinoxime of formula (III), or one of its pharmaceutically acceptable salts:

(III)

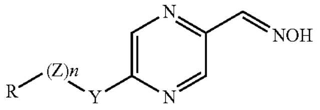

Preferably, Y is —$CH_2$—$CH_2$—, and n is 0, 1 or 2, preferably n is 0 or 2.

Preferably, R is a heteroaryl. Preferably said heteroaryl is not substituted. Preferably, said heteroaryl is a pyridine group such as 2-, 3- or 4-pyridino, preferably 3-pyridino.

Preferably, according to said second embodiment, the compounds of formula (III) and their salts are such that:

A is C,

B is —CH—,

X is N,

Y is —$CH_2$—$CH_2$—, n is 0, 1 or 2, preferably n is 0 or 2; and

R is a heteroaryl, preferably said heteroaryl is not substituted and is a pyridine group such as 2-, 3- or 4-pyridino, preferably 3-pyridino.

Preferably, the compound of formula (III) or one of its pharmaceutically acceptable salts is chosen from the following compounds:

(E)-5-(2-(pyridin-3-yl)ethyl)pyrazine-2-carbaldehyde oxime 13:

13

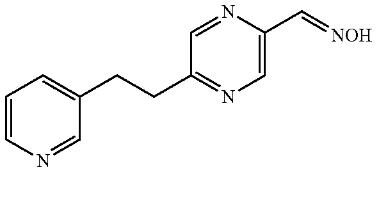

(E)-5-(2-(pyridin-3-yl)ethyl)pyrazine-2-carbaldehyde oxime hydrochloride NM-118:

NM-118

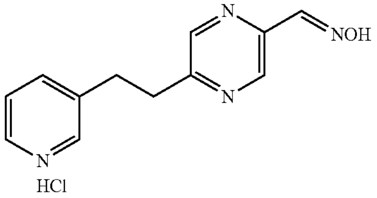

5-(4-(pyridin-3-yl)butyl)pyrazine-2-carbaldehyde oxime 17:

17

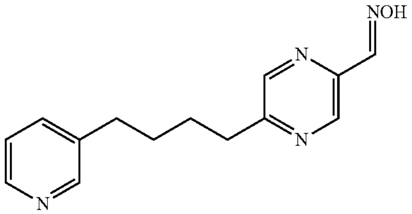

and (E)-5-(4-(pyridin-3-yl)butyl)pyrazine-2-carbaldehyde oxime hydrochloride NM-202:

NM-202

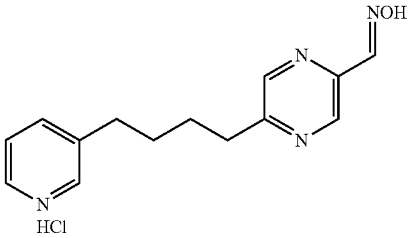

According to said third embodiment, it is preferred that the compound of the invention is a 5-substituted-2-pyrimidinoxime of formula (IV), or one of its pharmaceutically acceptable salts:

(IV)

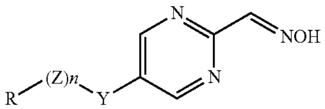

Preferably, Y is —$CH_2$—$CH_2$—, and n is 0, 1 or 2, preferably n is 0 or 2.

Preferably, R is a heteroaryl. Preferably said heteroaryl is not substituted. Preferably, said heteroaryl is a pyridine group such as 2-, 3- or 4-pyridino, preferably 3-pyridino.

Preferably, according to said third embodiment, the compounds of formula (IV) and their salts are such that:

A is C,

B is N,

X is —CH—,

Y is —$CH_2$—$CH_2$—, n is 0, 1 or 2, preferably n is 0 or 2; and

R is a heteroaryl, preferably said heteroaryl is not substituted and is a pyridine group such as 2-, 3- or 4-pyridino, preferably 3-pyridino.

Preferably, the compound of formula (IV) or one of its pharmaceutically acceptable salts is chosen from the following compounds:

(E)-5-(2-(pyridin-3-yl)ethyl)pyrimidine-2-carbaldehyde oxime 22:

22

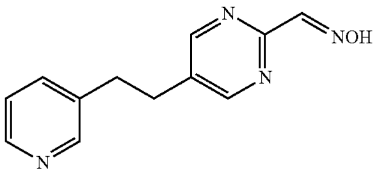

(E)-5-(2-(pyridin-3-yl)ethyl)pyrimidine-2-carbaldehyde oxime hydrochloride NM-158:

NM-158

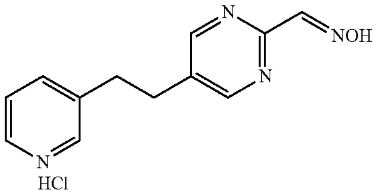

(E)-5-(4-(pyridin-3-yl)butyl)pyrimidine-2-carbaldehyde oxime:

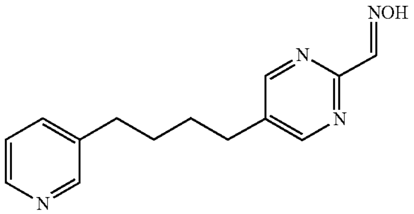

and (E)-5-(4-(pyridin-3-yl)butyl)pyrimidine-2-carbaldehyde oxime hydrochloride NM-251:

NM-251

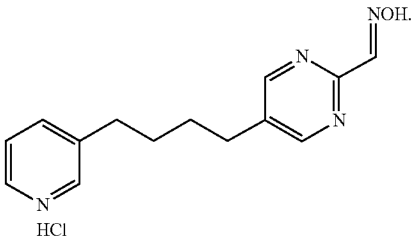

According to said fourth embodiment, it is preferred that the compound of the invention is a 6-substituted-4- pyridazinoxime of formula (V), or one of its pharmaceutically acceptable salts:

(V)

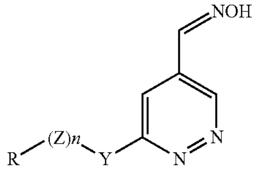

Preferably, Y is $-CH_2-CH_2-$, and n is 0, 1 or 2, preferably n is 0.

Preferably, R is a heteroaryl. Preferably said heteroaryl is not substituted. Preferably, said heteroaryl is a pyridine group such as 2-, 3- or 4-pyridino, preferably 3-pyridino.

Preferably, according to said fourth embodiment, the compounds of formula (V) and their salts are such that:

A is N,

B is C,

X is —CH—,

Y is $-CH_2-CH_2-$, n is 0, 1 or 2, preferably n is 0; and

R is a heteroaryl, preferably said heteroaryl is not substituted and is a pyridine group such as 2-, 3- or 4-pyridino, preferably 3-pyridino.

Preferably, the compound of formula (V) or one of its pharmaceutically acceptable salts is chosen from the following compounds:

(E)-6-(2-(pyridin-3-yl)ethyl)pyridazine-4-carbaldehyde oxime:

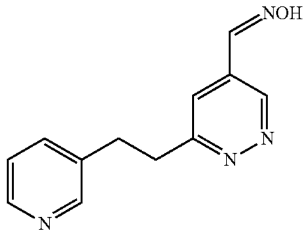

and (E)-6-(2-(pyridin-3-yl)ethyl)pyridazine-4-carbaldehyde oxime hydrochloride NM-279:

NM-279

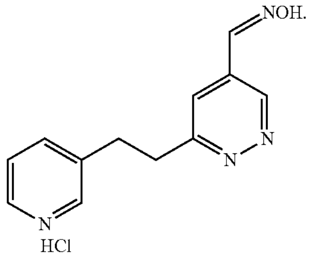

Preferably, the compound of formula (I) or one of its pharmaceutically acceptable salts is chosen from compounds of formula (II), (III), (IV) and (V) and their pharmaceutically acceptable salts.

More preferably, the compound of formula (I) or one of its pharmaceutically acceptable salts is chosen from:

(E)-6-(pyridin-3-ylethynyl)pyridazine-3-carbaldehyde oxime 4:

4

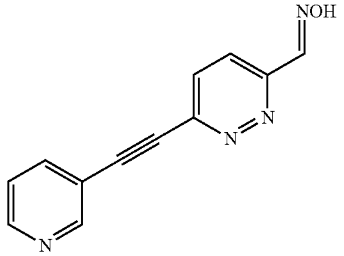

(E)-6-(pyridin-3-ylethynyl)pyridazine-3-carbaldehyde oxime hydrochloride NM-45:

NM-45

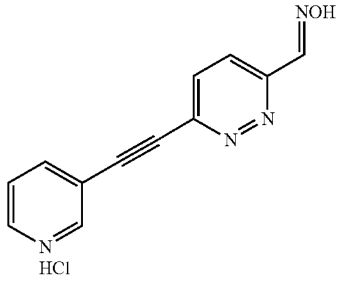

(E)-6-(2-(pyridin-3-yl)ethyl)pyridazine-3-carbaldehyde oxime 5:

5

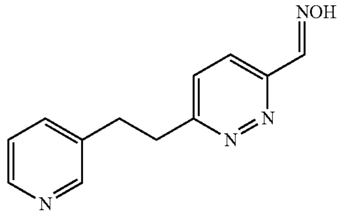

(E)-6-(2-(pyridin-3-yl)ethyl)pyridazine-3-carbaldehyde oxime hydrochloride NM-65:

NM-65

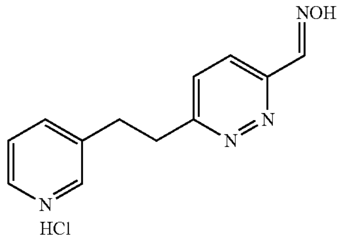

(E/Z)-6-(4-(pyridin-3-yl)but-1-ynyl)pyridazine-3-carbaldehyde oxime 7:

7

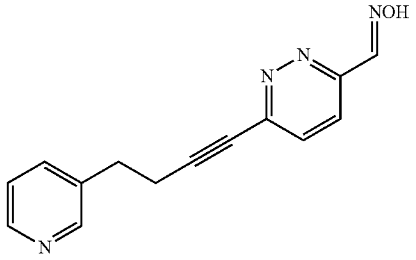

(E/Z)-6-(4-(pyridin-3-yl)but-1-ynyl)pyridazine-3-carbaldehyde oxime hydrochloride NM-184:

NM-184

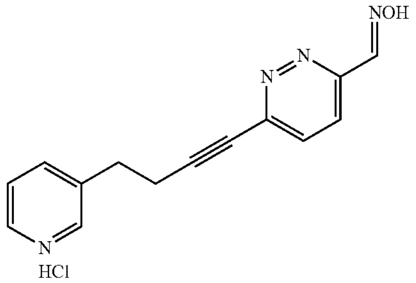

(E/Z)-6-(4-(pyridin-3-yl)butyl)pyridazine-3-carbaldehyde oxime 8:

8

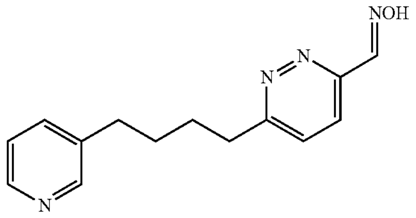

(E/Z)-6-(4-(pyridin-3-yl)butyl)pyridazine-3-carbaldehyde hydrochloride NM-201:

NM-201

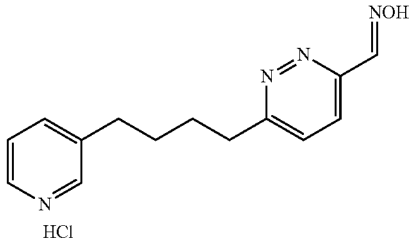

(E)-5-(2-(pyridin-3-yl)ethyl)pyrazine-2-carbaldehyde oxime 13:

13

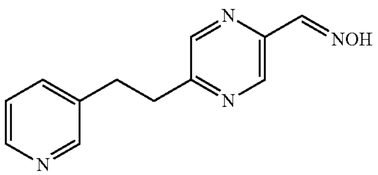

(E)-5-(2-(pyridin-3-yl)ethyl)pyrazine-2-carbaldehyde oxime hydrochloride NM-118:

NM-118

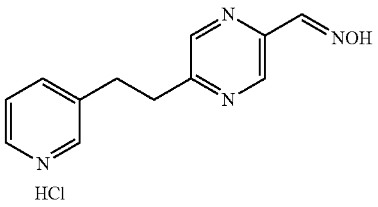

5-(4-(pyridin-3-yl)butyl)pyrazine-2-carbaldehyde oxime 17:

17

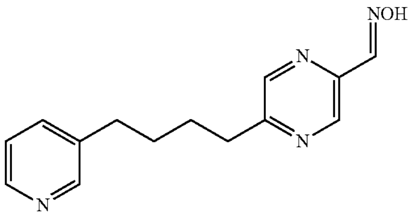

(E)-5-(4-(pyridin-3-yl)butyl)pyrazine-2-carbaldehyde oxime hydrochloride NM-202:

NM-202

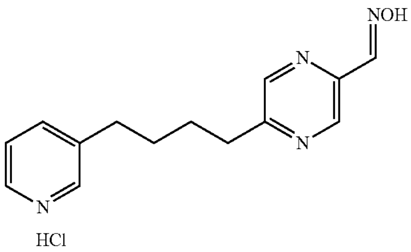

(E)-5-(2-(pyridin-3-yl)ethyl)pyrimidine-2-carbaldehyde oxime 22:

22

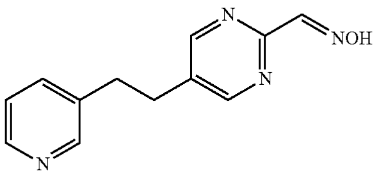

and (E)-5-(2-(pyridin-3-yl)ethyl)pyrimidine-2-carbaldehyde oxime hydrochloride NM-158:

NM-158

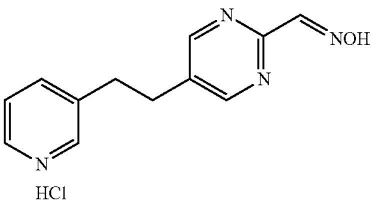

(E)-5-(4-(pyridin-3-yl)butyl)pyrimidine-2-carbaldehyde oxime:

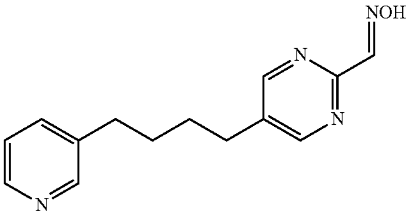

(E)-5-(4-(pyridin-3-yl)butyl)pyrimidine-2-carbaldehyde oxime hydrochloride NM-251:

NM-251

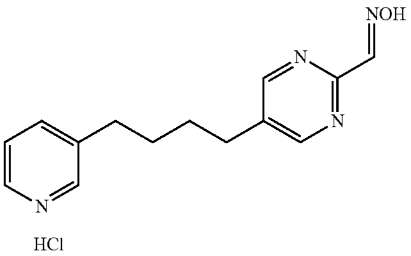

(E)-6-(2-(pyridin-3-yl)ethyl)pyridazine-4-carbaldehyde oxime:

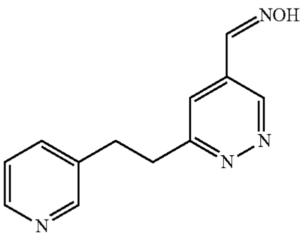

(E)-6-(2-(pyridin-3-yl)ethyl)pyridazine-4-carbaldehyde oxime hydrochloride NM-279:

NM-279

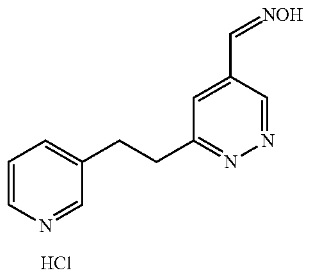

and (Z/E)-6-((1-methyl-1H-imidazol-5-yl)ethynyl)pyridazine-3-carbaldehyde oxime FR-156:

FR-156

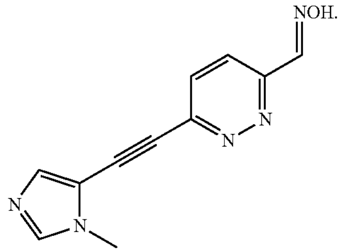

More preferably, the compound of formula (I) or one of its pharmaceutically acceptable salts is chosen from:

(E)-6-(pyridin-3-ylethynyl)pyridazine-3-carbaldehyde oxime hydrochloride NM-45:

NM-45

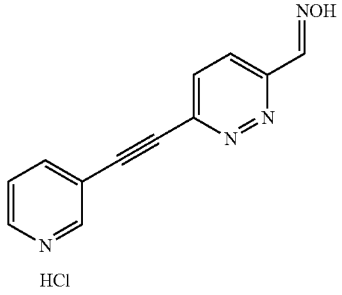

(E)-6-(2-(pyridin-3-yl)ethyl)pyridazine-3-carbaldehyde oxime hydrochloride NM-65:

NM-65

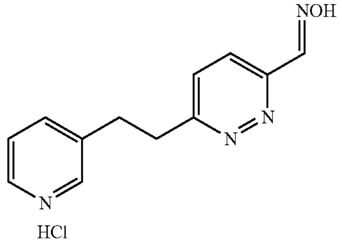

(E/Z)-6-(4-(pyridin-3-yl)but-1-ynyl)pyridazine-3-carbaldehyde oxime hydrochloride NM-184:

NM-184

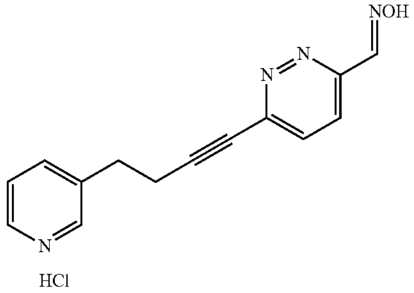

(E/Z)-6-(4-(pyridin-3-yl)butyl)pyridazine-3-carbaldehyde oxime hydrochloride NM-201:

NM-201

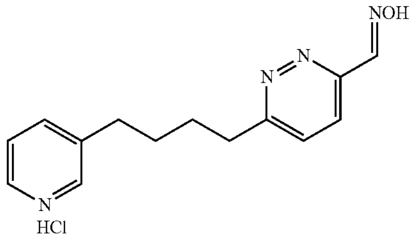

(E)-5-(2-(pyridin-3-yl)ethyl)pyrazine-2-carbaldehyde oxime hydrochloride NM-118:

NM-118

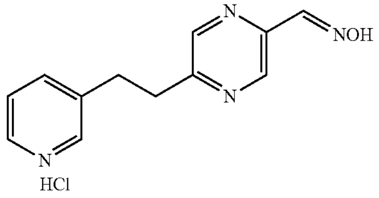

(E)-5-(4-(pyridin-3-yl)butyl)pyrazine-2-carbaldehyde oxime hydrochloride NM-202:

NM-202

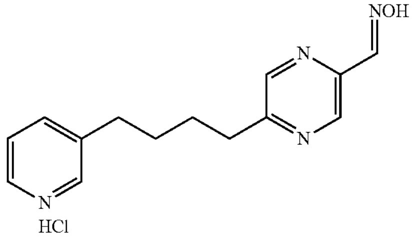

(E)-5-(2-(pyridin-3-yl)ethyl)pyrimidine-2-carbaldehyde oxime hydrochloride NM-158:

NM-158

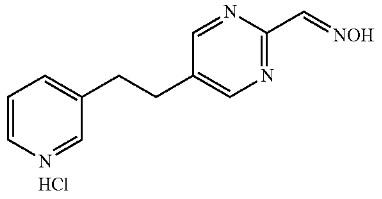

(E)-5-(4-(pyridin-3-yl)butyl)pyrimidine-2-carbaldehyde oxime hydrochloride NM-251:

NM-251

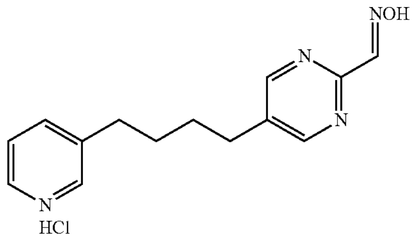

and (E)-6-(2-(pyridin-3-yl)ethyl)pyridazine-4-carbaldehyde oxime hydrochloride NM-279:

NM-279

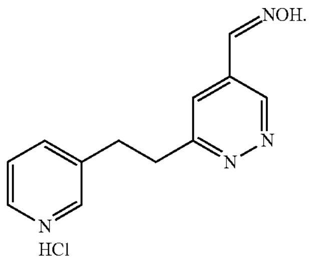

Preparation of the Compounds of Formula (I)

A compound of formula (I) according to the invention may be synthesized by any appropriate method. Such methods are exemplified in the following examples.

Preferably, the compounds of formula (I) are synthetized as described below. Such a process is chemoselective. Particularly, it does not necessitate any previous protection step of the oxime. Said process comprises a minimal number of steps, is quickly performed, at ambient temperature.

Notably a method of the invention may be as detailed in the following scheme:

Process to prepare compounds of formula (I), (II), (III) and (IV):

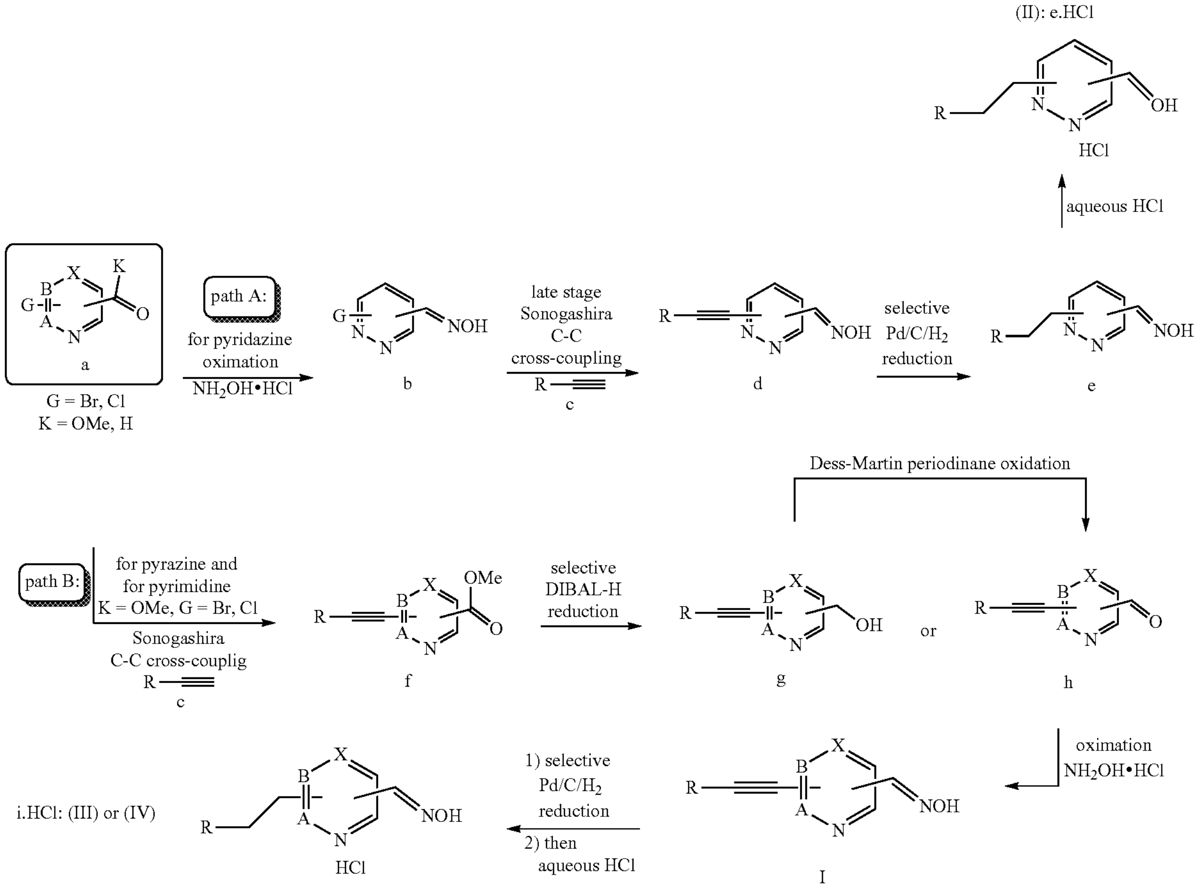

Process to prepare compounds of formula (IV) and (V):

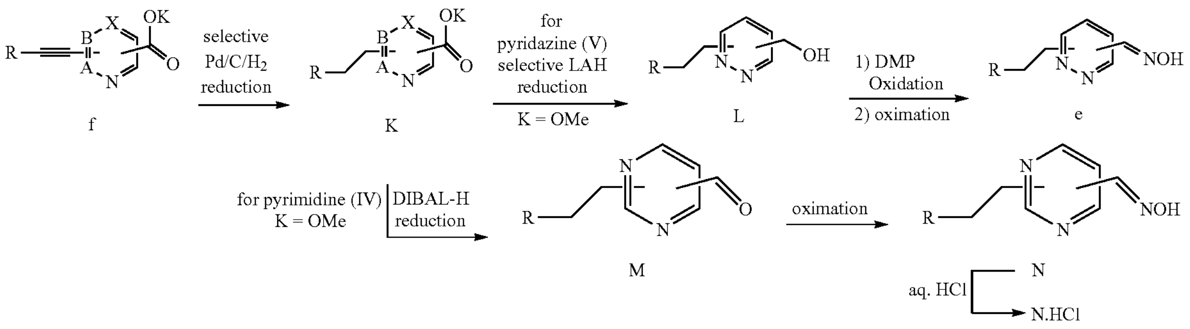

The main steps are as follows:

General route for the preparation of pyridazinoxime compound of formula (II): path A As shown in the scheme above, commercially available substrate a is first converted to the oxime upon treatment with hydroxylamine hydrochloride affording b. Subsequent late stage Sonogashira cross-coupling of b with alkyne c, yield the unsaturated reactivator d. Selective atmospheric pressure hydrogenation of the triple bond under Pd/C catalysis with hydrogen, afford reactivator e, that can be converted to the hydrochloric salt, after reaction with aqueous HCl leading to compounds of formula (II) e.HCl.

Alternatively, another path comprises the following steps for the preparation of pyridazinoxime compound of formula (V) (as it is the case for NM-279 of formula (V)): Commercially available substrate a is first submitted to a Sonogashira cross-coupling with alkyne c, to yield the unsaturated reactivator f comprising the —COK moiety (K being OMe). Selective atmospheric pressure hydrogenation of the triple bond under Pd/C catalysis with hydrogen, afford reactivator k comprising the —COK moiety. Then compound k is converted to the hydroxyl-compound L, and subsequently to the oxime e upon treatment with hydroxylamine hydrochloride. Reactivator e can be converted to the hydrochloric salt, after reaction with aqueous HCl leading to compounds of formula (V) e.HCl.

General Route for the Preparation of Pyrazine and Pyrimidine Compound of Formula (III) and (IV): Path B Halogenocarboxymethyl esters of pyrazine and pyrimidine starting building blocks a are first engaged in the Pd catalyzed Sonogashira cross-coupling reaction with the appropriate alkyne c, to afford coupled products f. Selective reduction of the methyl ester function of f using diisobutylaluminium hydride (DIBAL-H), lead to the fully reduced alcohol g, in the case of pyrazine. g is then converted to the aldehyde h using Dess-Martin periodinane reagent. Oximation of h upon treatment with hydroxylamine hydrochloride yield i. Final reaction of i with aqueous HCl afford compounds of formula (III) and (IV) i.HCl.

Alternatively, another path comprises the following steps for the preparation of pyrimidine compound of formula (IV) (as it is the case for NM-251 of formula (IV)):

Halogenocarboxymethyl esters of pyrimidine starting building blocks a are first engaged in the Pd catalyzed Sonogashira cross-coupling reaction with the appropriate alkyne c, to afford coupled products f. Selective atmospheric pressure hydrogenation of the triple bond of f under Pd/C catalysis with hydrogen, afford k (with single bonds only). Selective reduction of the methyl ester function of pyrimidine k using diisobutylaluminium hydride (DIBAL-H), leads to aldehyde M, which upon treatment with hydroxylamine hydrochloride yield pyrimidinoxime N (with single bonds only). Final reaction of N with aqueous HCl afford compounds of formula (IV) N.HCl (with single bonds only).

The method for preparing the compounds of the invention preferably comprises at least the following steps:

for the preparation of pyridazinoxime compounds of formula (II):

compound a

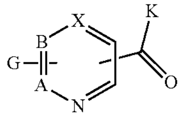

a is first converted to the corresponding oxime upon treatment with hydroxylamine hydrochloride, then a subsequent late stage Sonogashira cross-coupling of said oxime with alkyne c c is performed, in order to obtain the unsaturated pyridazine d of formula (I)

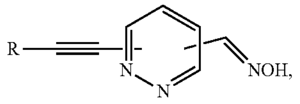

d and finally a selective atmospheric pressure hydrogenation of the triple bond is performed under Pd/C catalysis with hydrogen, to afford reactivator e of formula (I)

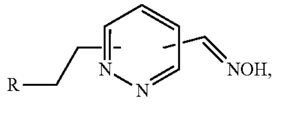

e that may optionally be converted into the corresponding salt, preferably the hydrochloric salt, for example after reaction with aqueous HCl, leading to compounds of formula (II) e.HCl;

for the preparation of pyridazinoxime compounds of formula (V): compound a a

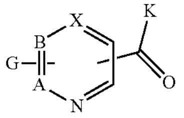

is first submitted to a late stage Sonogashira cross-coupling with alkyne c c in order to obtain the unsaturated reactivator f f

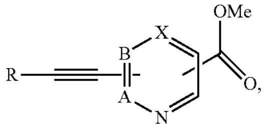

and a selective atmospheric pressure hydrogenation of the triple bond is performed under Pd/C catalysis with hydrogen, to afford reactivator k k

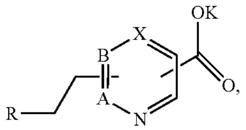

that is converted into the corresponding hydroxyl-compound, and subsequently to the oxime e upon treatment with hydroxylamine hydrochloride, optionally the oxime e is converted into the corresponding salt, preferably the hydrochloric salt, for example after reaction with aqueous HCl, leading to compounds of formula (V) e.HCl;

for the preparation of pyrazinoxime and pyrimidinoxime compounds of formula (III) and (IV):

compound a a

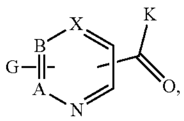

wherein K is —OMe and G is Br or Cl, is first engaged in the Pd catalyzed Sonogashira cross-coupling reaction with the appropriate alkyne c c

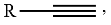

to afford coupled products, said coupled products are submitted to a selective reduction of the methyl ester function using DIBAL-H, in order to obtain the fully reduced alcohol in the case of pyrazine, said fully reduced alcohol is then converted into the corresponding aldehyde using Dess-Martin periodinane reagent, and finally oximation of the aldehyde, for example upon treatment with hydroxylamine hydrochloride, leads to a compound of the invention of formula (I) (compound i), optionally, final conversion of the compound of the invention of formula (I) into the corresponding salt, preferably the hydrochloric salt, for example after reaction with aqueous HCl, leads to compounds of formula (III) and (IV) i.HCl;

or alternatively for the preparation of pyrimidinoxime compounds of formula (IV):

compound a a

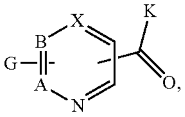

wherein K is —OMe and G is Br or Cl, is first engaged in the Pd catalyzed Sonogashira cross-coupling reaction with the appropriate alkyne c c to afford coupled products f, said coupled products are submitted to a selective atmospheric pressure hydrogenation of the triple bond of f under Pd/C catalysis with hydrogen, afford k k

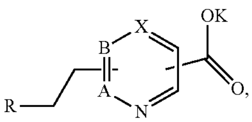

then k is submitted to a selective reduction of the methyl ester function, preferably using diisobutylaluminium hydride (DIBAL-H), to obtain the corresponding aldehyde M, which upon treatment with hydroxylamine hydrochloride leads to pyrimidinoxime N

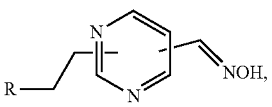

optionally pyrimidinoxime N is converted into the corresponding salt, preferably the hydrochloric salt, for example after reaction with aqueous HCl, leading to compounds of formula (IV) N·HCl.

Compounds d, e the salt of e, i and the salt of j, N and the salt of N, are all compounds of formula (I) of the invention.

Pharmaceutical Uses of the Compounds of the Invention

The compounds of this invention may be used in the treatment of a nervous and/or respiratory failure due to intoxication with at least one organophosphorous nerve agent which may preferably be selected from warfare agents such as O-ethyl S-[2-(diisopropylamino)ethyl] methylphosphonothioate (VX), tabun, sarin, cyclosarin and soman and pesticides such as paraoxon, parathion and tetraethyl pyrophosphate (TEPP). The compounds of the invention may be used in the treatment of a nervous and/or respiratory failure due to intoxication with at least one organophosphorous nerve agent, by virtue of their reactivation potency of organophosphorous inhibited cholinesterases, including acetylcholinesterase and butyrylcholinesterase. These compounds may alternatively be used in the treatment of diseases, which involve a reduced production of acetylcholine that may be overcome by the administration of acetylcholinesterase inhibitors. Examples of such diseases include in particular neurological diseases such as Alzheimer's disease.

These compounds may alternatively be used in the treatment of cancer, thanks to their action as inhibitors of histone deacetylases (HDAC).

The compound of this invention is usually included in a pharmaceutical composition comprising at least one compound according to the invention and a pharmaceutically acceptable support.

The amount of compound of formula (I) in the composition according to the invention may vary in a broad range depending upon the patient, the mode of administration and the expected effect.

The compound or composition according to the invention can be administered orally or non-orally, for instance via topical, parenteral, intramuscular, intravenous, cutaneous, nasal or rectal route.

The pharmaceutical composition of the invention can present different forms including granules, powders, tablets, capsules, syrups, emulsions, suspensions, and forms used for non-oral administration, for instance injections, sprays, transdermal patches or suppositories. These pharmaceutical forms can be prepared via known conventional techniques.

The preparation of an orally administered solid pharmaceutical form can be for instance performed by the following process: an excipient (for example lactose, sucrose, starch or mannitol), a desintegrant (for example calcium carbonate, calcium carboxymethylcellulose, alginic acid, sodium carboxymethylcellulose, colloidal silicon dioxide, sodium croscarmellose, crospovidone, guar gum, magnesium aluminium silicate, microcrystalline cellulose, cellulose powder, pregelatinised starch, sodium alginate or starch glycolate), a binder (for example alpha-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose or guar gum) and a lubricant (for example talc, magnesium stearate or polyethylene 6000) are added to the active principle and the mixture obtained is then tabletted. If necessary, the tablet can be coated via the known techniques, in order to mask the taste (for example with cocoa powder, mint, borneol or cinnamon powder) or to allow enteric dissolution or sustained release of the active principles. Coating products that can be used are, for example, ethylcellulose, hydroxymethylcellulose, polyoxyethylene glycol, cellulose acetophthalate, hydroxypropylmethylcellulose phthalate and Eudragit® (methacrylic acid-acrylic acid copolymer), Opadry® (hydroxypropylmethylcellulose+macrogol+titanium oxide+lactose monohydrate). Pharmaceutically acceptable colorants may be added (for example yellow iron oxide, red iron oxide or quinoline yellow lake).

Liquid pharmaceutical forms for oral administration include solutions, suspensions and emulsions. The aqueous solutions can be obtained by dissolving the active principle in water, followed by addition of flavourings, colorants, stabilisers and/or thickeners, if necessary. In order to improve the solubility, it is possible to add ethanol, propylene glycol or any other pharmaceutically acceptable non-aqueous solvent. The aqueous suspensions for oral use can be obtained by dispersing the finely divided active principle in water with a viscous product, such as a natural or synthetic gum or resin, methylcellulose or sodium carboxymethylcellulose.

The pharmaceutical forms for injection can be obtained, for example, by the following process. The active principle is dissolved, suspended or emulsified either in an aqueous medium (for example distilled water, physiological saline or Ringer's solution) or in an oily medium (for example olive oil, sesame seed oil, cottonseed oil, corn oil or propylene glycol), with a dispersant (for example Tween® 80, HCO® 60 (Nikko Chemicals), polyethylene glycol, carboxymethylcellulose or sodium alginate), a preserving agent (for example methyl p-hydroxybenzoate, propyl p-hydroxybenzoate, benzyl alcohol, chlorobutanol or phenol), an isotonicity agent (for example sodium chloride, glycerol, sorbitol or glucose) and optionally other additives, such as, if desired, a solubilizing agent (for example sodium salicylate or sodium acetate) or a stabilizer (for example human serum albumin).

Pharmaceutical forms for external use (topical use) can be obtained from a solid, semi-solid or liquid composition containing the active principle. For example, to obtain a solid form, the active principle can be treated with excipients (for example lactose, mannitol, starch, microcrystalline cellulose or sucrose) and a thickener (for example natural gums, cellulose derivatives or acrylic polymers) so as to convert them into powder. The liquid pharmaceutical compositions are prepared in substantially the same way as the forms for injection, as indicated previously. The semi-solid pharmaceutical forms are preferably in the form of aqueous or oily gels or in the form of pomades. These compositions may optionally contain a pH regulator (for example carbonic acid, phosphoric acid, citric acid, hydrochloric acid or sodium hydroxide) and a preserving agent (for example a p-hydroxybenzoic acid ester, chlorobutanol or benzalkonium chloride).

A method for the treatment of a nervous and/or respiratory failure due to intoxication with at least one organophosphorous nerve agent, comprising administering at least one compound according to the invention is also described herein.

A method for the treatment of a neurological disease such as Alzheimer's disease, comprising administering at least one compound according to the invention is also described herein.

A method for the treatment of a cancer, comprising administering at least one compound according to the invention is also described herein.

A method for the treatment of a virus, comprising administering at least one compound according to the invention is also described herein.

Within the context of the invention, the term treatment denotes curative, symptomatic, and/or preventive treatments. In particular, it can refer to reducing the progression of the disease, reducing or suppressing at least one of its symptoms or complications, or improving in any way the state of health of patients.

The administration of the compounds or of the composition according to the invention may be performed before, during or after the exposition of the subject to the organophosphorous nerve agent.

In the present invention, the terms “subject” and “patient” are used indifferently and designate a human subject.

The amount of compound according to the invention to be administered according to the invention may vary in a broad range depending upon the patient, the mode of administration and the expected effect. In particular, the amount of compound according to the invention may be comprised between 200 mg and 4000 mg, with up to 3 daily intakes.

The compound or composition according to the invention may be co-administered with at least one other active agent, such as an antimuscarinic agent, in particular atropine, an anticonvulsant, in particular diazepam or one of its prodrugs, such as avizafone, and/or a bioscavenger able to capture and/or degrade OPNAs in blood, such as human butyrylcholinesterase.

The term co-administered means that the administration of the compound or composition according to the invention and that of the other active agent can be simultaneous, sequential and/or separate.

Other Uses of the Compounds of the Invention

The compounds of this invention may further be used as tools for in vivo and/or in vitro biological studies. In this application, the compounds according to the invention may include one or more isotopes, which will allow for their detection.

The following examples are provided as illustrative, and not limitative, of the present invention.

EXAMPLES

Example 1: Synthesis of Compounds of the Invention (E)-6-(2-(pyridin-3-yl)ethyl)pyridazine-3-carbaldehyde oxime hydrochloride NM-65

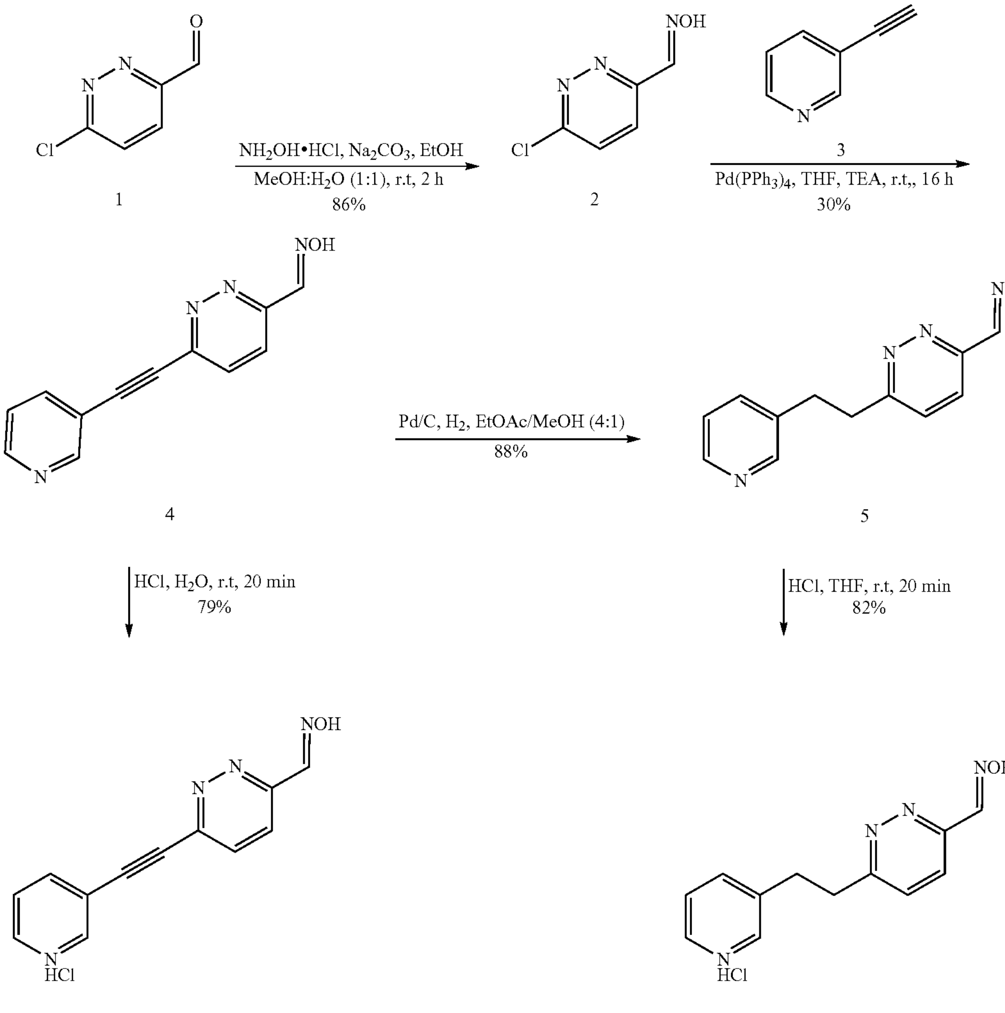

1

2

3

4

5

NM-45

NM-65

(E)-6-chloropyridazine-3-carbaldehyde oxime 2

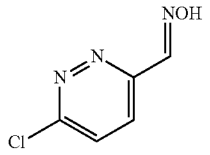

2

A solution of commercially available 6-chloropyridazine-3-carbaldehyde (200 mg, 1.403 mmol, 1 equiv), hydroxylamine hydrochloride (146 mg, 2.105 mmol, 1.5 equiv), and $Na_2CO_3$ (446 mg, 4.210 mmol, 3 equiv) in 1:1 ratio of MeOH/$H_2O$ (10 mL) was stirred at room temperature for 2 h. After completion (checked by TLC), MeOH was distilled off under reduced pressure and extracted with EtOAc (10 mL×3), washed with brine (10 mL) and water (10 mL). The organic layers dried over anhydrous $Na_2SO_4$ and distilled under reduced pressure, and the residue was purified by column chromatography (EtOAc/PE 30:70) to afford the (E)-6-chloropyridazine-3-carbaldehyde oxime as an off white solid (190 mg, 86%); $R_f$ (30% EtOAc/PE) 0.3; $^1$H NMR (400 MHz, DMSO): δ ppm 12.28 (s, 1H), 8.35 (d, J=0.7 Hz, 1H), 8.08 (d, J=9.0 Hz, 1H), 7.93 (dd, J=9.0, 0.7 Hz, 1H); $^{13}$C NMR (101 MHz, DMSO): δ ppm 156.47, 155.51, 146.21, 129.75, 126.85.

(E)-6-(pyridin-3-ylethynyl)pyridazine-3-carbaldehyde oxime 4

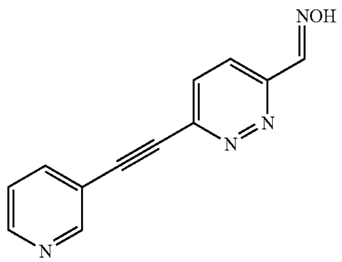

4

To a degassed solution of (E)-6-chloropyridazine-3-carbaldehyde oxime 2 (50.3 mg, 0.291 mmol, 1.1 equiv) in THF/$Et_3N$ (4 mL/2 mL), $Pd[PPh_3]_4$ (50.5 mg, 0.043 mmol, 0.15 equiv) and CuI (16.6 mg, 0.0873 mmol, 0.3 equiv) were added. After degassing the reaction mixture for 5 min at room temperature, 3-ethynylpyridine 3 (30 mg, 0.291 mmol, 1 equiv) in THF (2 mL) was added dropwise and the reaction mixture was stirred at the room temperature for 16 h. After completion (checked by TLC), the reaction mixture was concentrated under reduced pressure and the residue was purified by column chromatography to afford (E)-6-(pyridin-3-ylethynyl)pyridazine-3-carbaldehyde oxime 4 as an off white solid (20 mg, 30.6%); $R_f$ (50% EtOAc/PE) 0.2; HRMS (ESI$^+$): m/z calcd for $C_{12}H_9N_4O^+$ 225.0759 found 225.0771; $^1$H NMR (400 MHz, DMSO): δ ppm 12.31 (s, 1H), 8.94-8.85 (m, 1H), 8.74-8.66 (m, 1H), 8.41 (s, 1H), 8.14 (dt, J=7.9, 1.8 Hz, 1H), 8.09 (d, J=8.8 Hz, 1H), 8.02-7.96 (m, 1H), 7.59-7.50 (m, 1H); $^{13}$C NMR (101 MHz, DMSO): δ ppm 153.76, 152.10, 150.22, 146.58, 146.36, 139.25, 130.63, 123.84, 122.97, 117.93, 90.54, 88.90.

(E)-6-(pyridin-3-ylethynyl)pyridazine-3-carbaldehyde oxime hydrochloride NM-45

NM-45

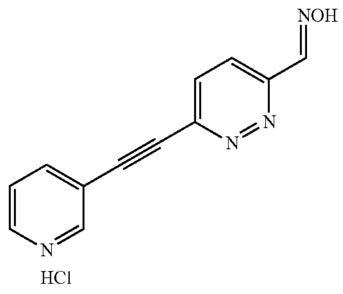

To a solution of (E)-6-(pyridin-3-ylethynyl)pyridazine-3-carbaldehyde oxime 4 (12 mg, 0.053 mmol) in water (2 ml) was added 2N HCl (0.5 mL) at room temperature and stirred for 20 min at same temperature. Upon completion, solvent was distilled off under reduced pressure and the resulting solid was washed with diethyl ether (2×3 mL). The solid was dried under vacuum to give (E)-6-(pyridin-3-ylethynyl)pyridazine-3-carbaldehyde oxime hydrochloride NM-45 as a light brown solid (11 mg, 79%). $^1$H NMR (500 MHz, DMSO-$d_6$): δ ppm 12.29 (s, 1H), 9.30-9.18 (m, 1H), 8.68 (d, J=7.7 Hz, 1H), 8.46-8.35 (m, 1H), 8.28 (d, J=8.9 Hz, 1H), 8.14 (d, J=8.8 Hz, 1H), 8.08-7.91 (m, 2H).

(E)-6-(2-(pyridin-3-yl)ethyl)pyridazine-3-carbaldehyde oxime 5

5

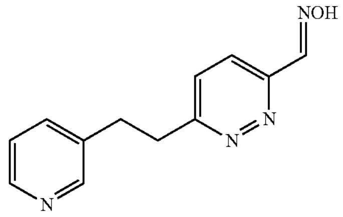

To a solution of (E)-6-(pyridin-3-ylethynyl)pyridazine-3-carbaldehyde oxime 4 (18 mg, 0.141 mmol) in 4:1 ratio of EtOAc/MeOH (5 mL) was added 10% Pd/C (10 mg) at room temperature under Argon atmosphere and stirred the mixture for 2 h. Upon completion, the mixture was filtered using celite pad concentrated under reduced pressure to afford cis-trans mixture of 6-(2-(pyridin-3-yl)ethyl)pyridazine-3-carbaldehyde oxime 5 as a white solid (16 mg, 88%); $R_f$ (EtOAc) 0.25; HRMS (ESI$^+$): m/z calcd for $C_{12}H_{13}N_4O^+$ 229.108853 found 229.108387; $^1$H NMR (500 MHz, Acetone-$d_6$): δ ppm 10.97 (s, 1H), 8.35 (d, J=2.3 Hz, 1H), 8.27 (dd, J=4.8, 1.7 Hz, 1H), 8.22 (d, J=0.8 Hz, 1H), 7.79 (d, J=8.8 Hz, 1H), 7.54 (dt, J=7.7, 2.0 Hz, 1H), 7.42 (dd, J=8.9, 0.7 Hz, 1H), 7.13 (ddd, J=7.8, 4.7, 0.9 Hz, 1H), 3.20 (t, J=10 Hz, 2H), 3.04 (t, J=10 Hz, 2H); $^{13}$C NMR (126 MHz, Acetone-$d_6$): δ ppm 162.46, 153.92, 150.01, 147.55, 147.44, 136.40, 135.73, 126.82, 123.25, 122.86, 37.02, 31.88.

(E)-6-(2-(pyridin-3-yl)ethyl)pyridazine-3-carbaldehyde oxime hydrochloride NM-65

NM-65

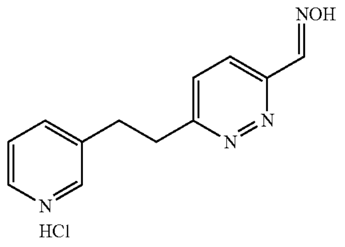

To a solution of (E)-6-(2-(pyridin-3-yl)ethyl)pyridazine-3-carbaldehyde oxime 5 (14 mg, 0.061 mmol) in THF (3 ml) was added 2N HCl (0.5 mL) at room temperature and stirred for 30 min at same temperature. Upon completion, solvent was distilled off under reduced pressure and the resulting solid was washed with diethyl ether. The solid was dried under vacuum to give (E)-6-(2-(pyridin-3-yl)ethyl) pyridazine-3-carbaldehyde oxime hydrochloride as a light brown solid NM-65 (13.8 mg, 82%); $^{1}$H NMR (500 MHz, $CD_3OD$): δ ppm 8.94 (d, J=2.0 Hz, 1H), 8.80 (dt, J=5.8, 1.1 Hz, 1H), 8.69 (dt, J=8.1, 1.7 Hz, 1H), 8.60 (d, J=8.9 Hz, 1H), 8.37 (s, 1H), 8.31 (d, J=8.9 Hz, 1H), 8.11 (dd, J=8.2, 5.8 Hz, 1H), 3.62-3.57 (m, 2H), 3.51-3.47 (m, 2H); $^{13}$C NMR (126 MHz, $CD_3OD$): δ ppm 162.30, 154.28, 147.13, 142.67, 141.31, 140.79, 139.66, 133.64, 129.82, 127.20, 33.90, 30.06.

(E/Z)-6-(4-(pyridin-3-yl)but-1-ynyl)pyridazine-3-carbaldehyde oxime hydrochloride NM-184

(E/Z)-6-(4-(pyridin-3-yl)butyl)pyridazine-3-carbaldehyde hydrochloride NM-201

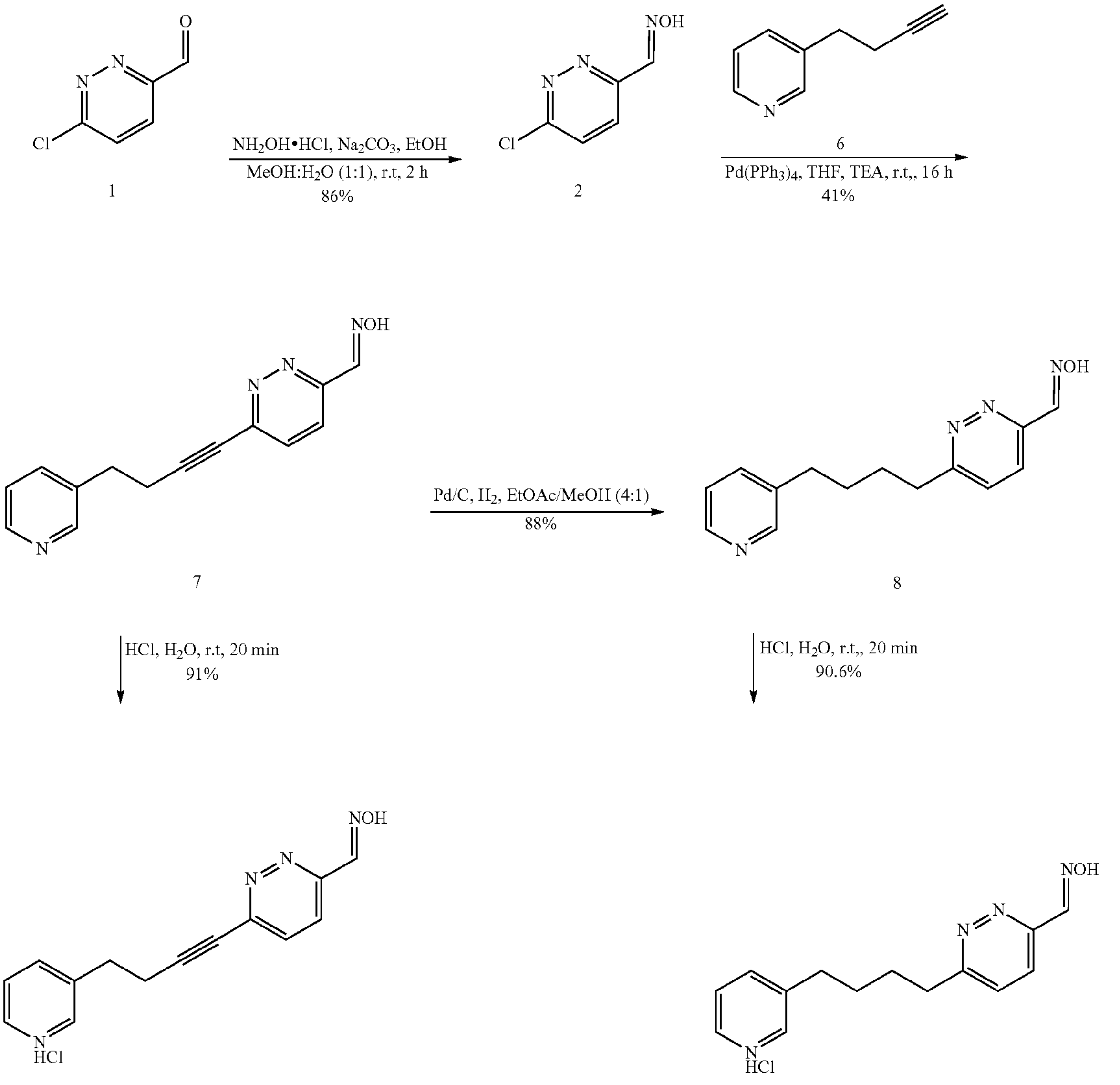

NM-184

NM-201

(E/Z)-6-(4-(pyridin-3-yl)but-1-ynyl)pyridazine-3-carbaldehyde oxime 7

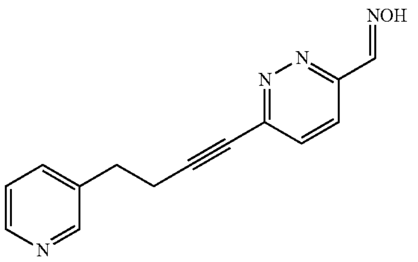

7

To a degassed solution of (E)-6-chloropyridazine-3-carbaldehyde oxime (131 mg, 0.834 mmol, 1.1 equiv) in THF/$Et_3N$ (9 mL/3 mL), $Pd[PPh_3]_4$ (132.4 mg, 0.114 mmol, 0.15 equiv) and CuI (43.6 mg, 0.228 mmol, 0.3 equiv) were added. After degassing the reaction mixture for 5 min at room temperature, 3-(but-3-ynyl)pyridine 6 (100 mg, 0.763 mmol, 1 equiv) in THF (2 mL) was added dropwise and the reaction mixture was stirred at the room temperature for 16 h. After completion (checked by TLC), the reaction mixture was concentrated under reduced pressure and the residue was purified by column chromatography to afford cis-trans mixture (8:2 ratio) of (E/Z)-6-(4-(pyridin-3-yl)but-1-ynyl) pyridazine-3-carbaldehyde oxime 7 as an off white solid (75 mg, 41%); $R_f$ (10% EtOAc) 0.3; HRMS ($ESI^+$): m/z calcd for $C_{14}H_{12}N_4NaO^+$ 275.090332 found 275.090899; $^1H$ NMR (400 MHz, Acetone); $^1H$ NMR (400 MHz, Acetone-$d_6$): δ ppm 11.26 (s, 1H), 8.64-8.56 (m, 1H), 8.46 (dd, J=4.8, 1.7 Hz, 1H), 8.38 (s, 0.8H), 7.98 (d, J=8.8 Hz, 0.8H), 7.84 (s, 0.2H), 7.79 (dt, J=7.7, 2.1 Hz, 1H), 7.71 (d, J=8.9 Hz, 0.2H), 7.60 (d, J=8.8 Hz, 1H), 7.32 (dd, J=7.8, 4.7 Hz, 1H), 3.02 (t, J=7.1 Hz, 2H), 2.95-2.85 (m, 2H); $^{13}C$ NMR (101 MHz, Acetone): δ ppm 153.44, 150.07, 147.84, 147.68, 135.89, 135.70, 131.83, 129.65, 123.29, 122.30, 94.83, 78.97, 31.15, 20.76.

(E/Z)-6-(4-(pyridin-3-yl)but-1-ynyl)pyridazine-3-carbaldehyde oxime hydrochloride NM-184

NM-184

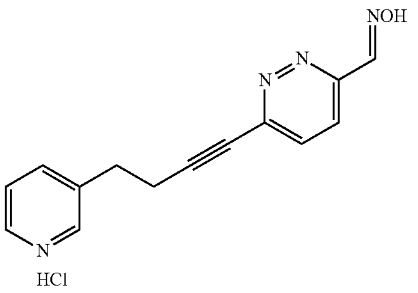

To a solution of (E)-6-(4-(pyridin-3-yl)but-1-ynyl) pyridazine-3-carbaldehyde oxime (12 mg, 0.475 mmol) in water (2 ml) was added 2N HCl (0.5 mL) at room temperature and stirred for 20 min at same temperature. Upon completion, solvent was distilled off under reduced pressure and the resulting solid was washed with diethyl ether. The solid was dried under vacuum to give cis-trans mixture of (7.5:2.5 ratio) (E/Z)-6-(4-(pyridin-3-yl)but-1-ynyl) pyridazine-3-carbaldehyde oxime hydrochloride as a brown solid (12.5 mg, 91%); $^{13}H$ NMR (400 MHz, $CD_3OD$): δ ppm 8.95 (bs, 1H), 8.83-8.69 (m, 3H), 8.43-8.37 (m, 1H), 8.15-8.04 (m, 1H), 7.15 (s, 0.75H), 7.03 (s, 0.25), 3.53-3.47 (m, 0.25H), 3.39 (t, J=7.4 Hz, 1.75H), 3.26-3.20 (m, 1.75H), 3.13 (t, 0.25); $^{13}C$ NMR (101 MHz, $CD_3OD$): δ ppm 155.17, 154.22, 147.31, 147.21, 146.14, 142.50, 141.29, 141.20, 141.03, 140.64, 139.61, 139.35, 133.30, 130.23, 127.20, 126.98, 123.56, 118.99, 40.98, 36.57, 29.91, 29.83.

(E/Z)-6-(4-(pyridin-3-yl)butyl)pyridazine-3-carbaldehyde oxime 8

8

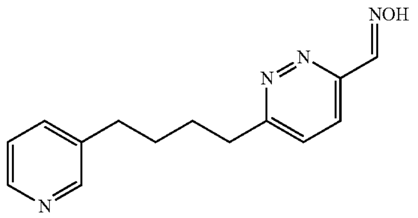

To a solution of (E/Z)-6-(4-(pyridin-3-yl)but-1-ynyl) pyridazine-3-carbaldehyde oxime 7 (20 mg, 0.792 mmol) in EtOAc (4 mL) was added 10% Pd/C (10 mg) at room temperature under $H_2$ atmosphere (balloon) and stirred the mixture for 2 h. Upon completion, the mixture was filtered using celite pad concentrated under reduced pressure. The crude was purified by column chromatography (100% AE) to afford cis-trans (94:6 ratio) (E-Z)-6-(4-(pyridin-3-yl) butyl)pyridazine-3-carbaldehyde oxime 8 as a white solid (18 mg, 88.6%); $R_f$ (100% EtOAc) 0.25; HRMS ($ESI^+$): m/z calcd for $C_{14}H_{16}N_4NaO$ 279.121632 found 279.122374; $^1H$ NMR (500 MHz, 126 MHz, $CD_3OD$): δ ppm 8.55 (d, J=8.8 Hz, 0.06H), 8.35-8.22 (m, 2H), 8.19 (s, 0.94H), 7.94 (d, J=8.8 Hz, 0.94H), 7.63 (s, 0.06H), 7.59 (dt, J=7.9, 1.9 Hz, 1H), 7.57 (d, J=8.8 Hz, 0.06H), 7.50 (d, J=8.8 Hz, 0.94H), 7.24 (dd, J=7.9, 4.8 Hz, 1H), 2.91 (t, J=7.6 Hz, 2H), 2.62 (t, J=7.6 Hz, 2H), 1.78-1.67 (m, 2H), 1.67-1.58 (m, 2H); $^{13}C$ NMR (126 MHz, $CD_3OD$): δ ppm 163.90, 163.48, 154.19, 151.23, 148.63, 146.15, 145.92, 142.66, 138.46, 136.87, 129.87, 127.78, 127.29, 124.18, 123.78, 34.94, 32.01, 31.67, 30.29, 29.35, 28.60.

(E/Z)-6-(4-(pyridin-3-yl)butyl)pyridazine-3-carbaldehyde oxime hydrochloride NM-201

NM-201

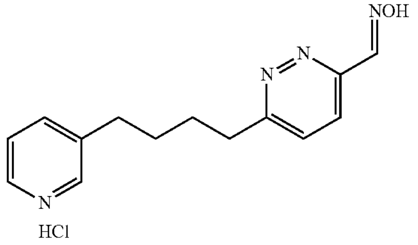

To a solution of (E/Z)-6-(4-(pyridin-3-yl)butyl) pyridazine-3-carbaldehyde oxime (14 mg, 0.061 mmol) was added 2N HCl (0.2 mL) at room temperature and stirred for 30 min at same temperature. Upon completion, solvent was distilled off under reduced pressure and the resulting solid was washed with diethyl ether (3 mL×2). The solid was dried under vacuum to give cis-trans mixture (90:10 ratio) of (E/Z)-6-(4-(pyridin-3-yl)butyl)pyridazine-3-carbaldehyde oxime hydrochloride NM-201 as a pale yellow solid (14.5 mg, 90.6%); $^1$H NMR (500 MHz, $CD_3OD$): δ ppm 8.86 (s, 1H), 8.80-8.76 (m, 2H), 8.62 (m, 1.2H), 8.50 (d, J=8.9 Hz, 0.9H), 8.35 (s, 0.9H), 8.08 (dd, J=8.1, 5.7 Hz, 1H), 3.29 (t, J=7.5 Hz, 2H), 3.02 (t, J=7.6 Hz, 2H), 2.01-1.90 (m, 4H); $^{13}$C NMR (126 MHz, $CD_3OD$): δ ppm 163.50, 155.49, 146.98, 142.76, 142.67, 140.89, 139.07, 135.08, 132.66, 127.09, 32.19, 31.54, 29.41, 27.44.

(E)-5-(2-(pyridin-3-yl)ethyl)pyrazine-2-carbaldehyde oxime hydrochloride NM-118

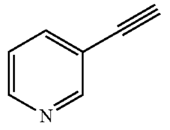

3

+

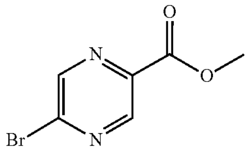

9

Pd($PPh_3$)$_4$,
CuI, TEA
THF, r.t,
16 h
55%

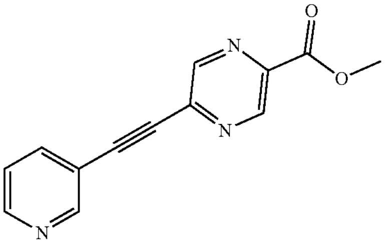

10

Pd/C,
MeOH,
$H_2$
r.t, 12 h
90%

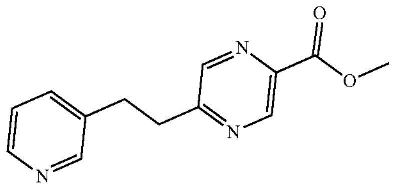

11

LAH,
THF,
0° C.-r.t,
6 h
30%

-continued

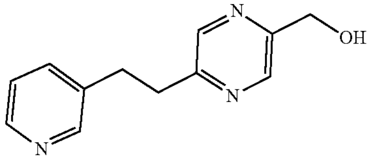

12

Dess Martin
periodinane,
$CH_2Cl_2$,
r.t, 2 h
NaOAc,
$NH_2OH$•
HCl, EtOH,
80° C., 12 h
75.4%

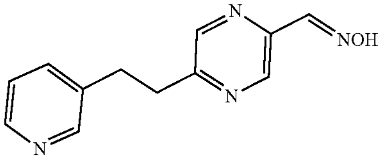

13

HCl,
$CH_2Cl_2$,
r.t,
20 min
80%

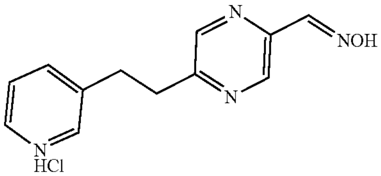

NM-118

Methyl 5-(pyridin-3-ylethynyl)pyrazine-2-carboxylate 10

10

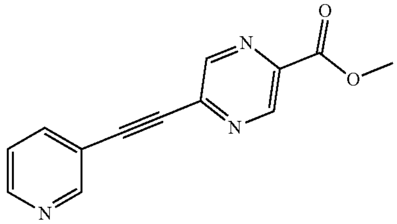

To a degassed solution of methyl methyl 5-bromopyrazine-2-carboxylate 9 (231 mg, 1.066 mmol, 1.1 equiv) in THF/$Et_3N$ (9 mL/3 mL), Pd[$PPh_3$]$_4$ (168.4 mg, 0.144 mmol, 0.15 equiv) and CuI (55.46 mg, 0.29 mmol, 0.3 equiv) were added. After degassing the reaction mixture for 5 min at room temperature, 3-ethynylpyridine (100 mg, 0.97 mmol, 1 equiv) was added dropwise and the reaction mixture was stirred at the room temperature for 16 h. Upon completion, the reaction mixture was concentrated under reduced pressure and the residue was purified by column chromatography (EtOAc/PE, 1:1) to afford methyl 5-(pyridin-3-ylethynyl)pyrazine-2-carboxylate 10 as a pale yellow solid (130 mg, 55%); $R_f$ (50% EtOAc/PE) 0.2; HRMS (ESI$^+$): m/z calcd for $C_{13}H_{10}N_3O_2^+$ 240.076753 found 240.076326 $^1$H NMR (400 MHz, $CDCl_3$): δ ppm 9.24 (d, J=1.5 Hz, 1H), 8.88-8.74 (m, J=4.8 Hz, 2H), 8.60 (s, 1H), 7.88 (dt, J=7.9, 1.8 Hz, 1H), 7.31 (dd, J=7.9, 4.8 Hz, 1H) 3.99 (s, 3H); $^{13}$C NMR (101 MHz, $CDCl_3$): δ ppm 163.92, 152.68, 150.13, 146.93, 145.83, 142.32, 140.92, 139.31, 92.56, 88.68, 53.30.

Methyl 5-(2-(pyridin-3-yl)ethyl)pyrazine-2-carboxylate 11

11

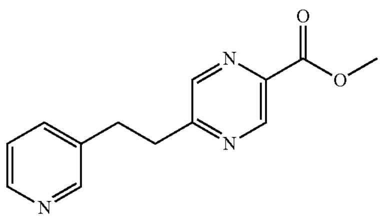

To a solution of methyl 5-(pyridin-3-ylethynyl)pyrazine-2-carboxylate 10 (105 mg, 0.438 mmol) in MeOH (10 mL) was added 10% Pd/C (60 mg) at room temperature under Argon atmosphere and stirred the mixture for 12 h under $H_2$ atmosphere using balloon pressure. Upon completion, the mixture was filtered using small celite pad, concentrated under reduced pressure and purified by $SiO_2$ column chromatography (EtOAc/PE, 7:3) to afford methyl 5-(2-(pyridin-3-yl)ethyl)pyrazine-2-carboxylate 11 as light brown syrup (96 mg, 90%); $R_f$ (50% EtOA/PE) 0.3; HRMS (ESI$^+$): m/z calcd for $C_{13}H_{14}N_3O_2^+$ 244.108053 found 244.110315; $^1$H NMR (400 MHz, $CDCl_3$): δ ppm 9.22 (s, 1H), 8.81-8.16 (m, 3H), 7.47 (d, J=7.7 Hz, 1H), 7.21 (s, 1H), 4.00 (s, 3H), 3.23-3.10 (dt, J=14.3, 6.6 Hz, 4H); $^{13}$C NMR (101 MHz, $CDCl_3$) δ ppm 164.35, 159.36, 149.66, 147.72, 145.45, 143.87, 140.89, 135.63, 52.90, 36.56, 31.73.

(5-(2-(pyridin-3-yl)ethyl)pyrazin-2-yl)methanol 12

12

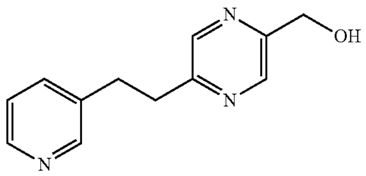

To a solution of $LiAlH_4$ (35 mg, 0.922 mmol) in THF (3 mL) at 0° C. was added methyl 5-(2-(pyridin-3-yl)ethyl) pyrazine-2-carboxylate 10 (90 mg, 0.369 mmol) in THF (2 mL) dropwise and stirred for 6 h at room temperature. Upon completion, the mixture was quenched with Fisher method and filtered the white aluminum salts. The filtrates were concentrated and purified by $SiO_2$ column chromatography (100% EtOAc) to give (5-(2-(pyridin-3-yl)ethyl)pyrazin-2-yl)methanol 12 as a light brown colour solid (22 mg, 30%); $R_f$0.3 (10% MeOH in $CH_2Cl_2$); HRMS (ESI$^+$): m/z calcd for $C_{12}H_{14}N_3O$ 216.113139 found 216.112191 $^1$H NMR (400 MHz, $CDCl_3$) δ ppm 8.62 (s, 1H), 8.49-833 (m, 2H), 8.29 (d, J=1.0 Hz, 1H), 7.51 (d, J=7.8 Hz, 1H), 7.22 (dd, J=7.6, 4.8 Hz, 1H), 4.81 (s, 2H), 3.18-3.06 (m, 4H); $^{13}$C NMR (101 MHz, $CDCl_3$) δ ppm 154.21, 152.89, 149.71, 147.56, 142.93, 142.16, 136.06, 123.56, 62.80, 36.23, 32.30.

(E)-5-(2-(pyridin-3-yl)ethyl)pyrazine-2-carbaldehyde oxime 13

13

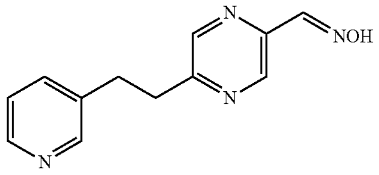

To a solution of (5-(2-(pyridin-3-yl)ethyl)pyrazin-2-yl) methanol (20 mg, 0.092 mmol) in $CH_2Cl_2$ (3 mL) was added dess-matin periodinane (47 mg, 0.110 mmols) and $NaHCO_3$ (18.7 mg, 0.222 mmols) at 0° C. and stirred for 2 h. Upon completion, filtered the mixture on small celite pad and concentrated. The crude was used in the next reaction without further purification. To a solution of (E)-5-(2-(pyridin-3-yl)ethyl)pyrazine-2-carbaldehyde in EtOH (4 mL) was added hydroxylamine hydrochloride (13 mg, 0.187 mmol), NaOAc (23 mg, 0.280 mmol) and refluxed for 16 h. After concentration by vacuo, the crude product was purified by $SiO_2$ column chromatography (100% EtOAc) to afford 3-hydroxy-6-(2-(pyridin-3-yl)ethyl)picolinaldehyde oxime as an off white solid (16 mg, 75.4%); $R_f$ 0.5%, (10% $MeOH/CH_2Cl_2$); $^1$H NMR (400 MHz, $CD_3OD$): δ 8.96 (d, J=1.3 Hz, 1H), 8.43-8.33 (m, 3H), 8.12 (s, 1H), 7.77-7.69 (m, 1H), 7.37 (dd, J=7.8, 4.9 Hz, 1H), 3.24-3.10 (m, 4H); $^{13}$C NMR (101 MHz, $CD_3OD$): δ ppm 155.45, 148.76, 146.51, 146.41, 145.95, 143.51, 141.06, 137.14, 137.03, 123.80, 35.61, 31.56.

(E)-5-(2-(pyridin-3-yl)ethyl)pyrazine-2-carbaldehyde oxime hydrochloride NM-118

NM-118

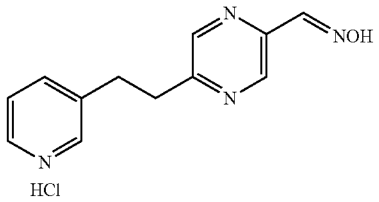

To a solution of (E)-5-(2-(pyridin-3-yl)ethyl)pyrazine-2-carbaldehyde oxime 13 (15 mg, 0.065 mmol) in $CH_2Cl_2$ (3 ml) was added 2N HCl (2 mL) at room temperature and stirred for 20 min at same temperature. Upon completion, solvent was distilled off under reduced pressure and the resulting solid was washed with diethyl ether (2×3 mL). The solid was dried under vacuum to give (E)-5-(2-(pyridin-3-yl)ethyl)pyrazine-2-carbaldehyde oxime hydrochloride NM-118 as a light brown solid (14 mg, 80%); $R_f$ 0.45% (10% $MeOH/CH_2Cl_2$); $C_{12}H_{13}N_4O^+$ 229.108387 found 229.107347; $^1$H NMR (400 MHz, $CD_3OD$): δ ppm 9.27-8.96 (m, 1H), 8.95-8.53 (m, 4H), 8.40-7.91 (m, 2H), 3.53-3.35 (m, 4H.

(E/Z)-5-(4-(pyridin-3-yl)butyl)pyrazine-2-carbaldehyde oxime hydrochloride NM-202

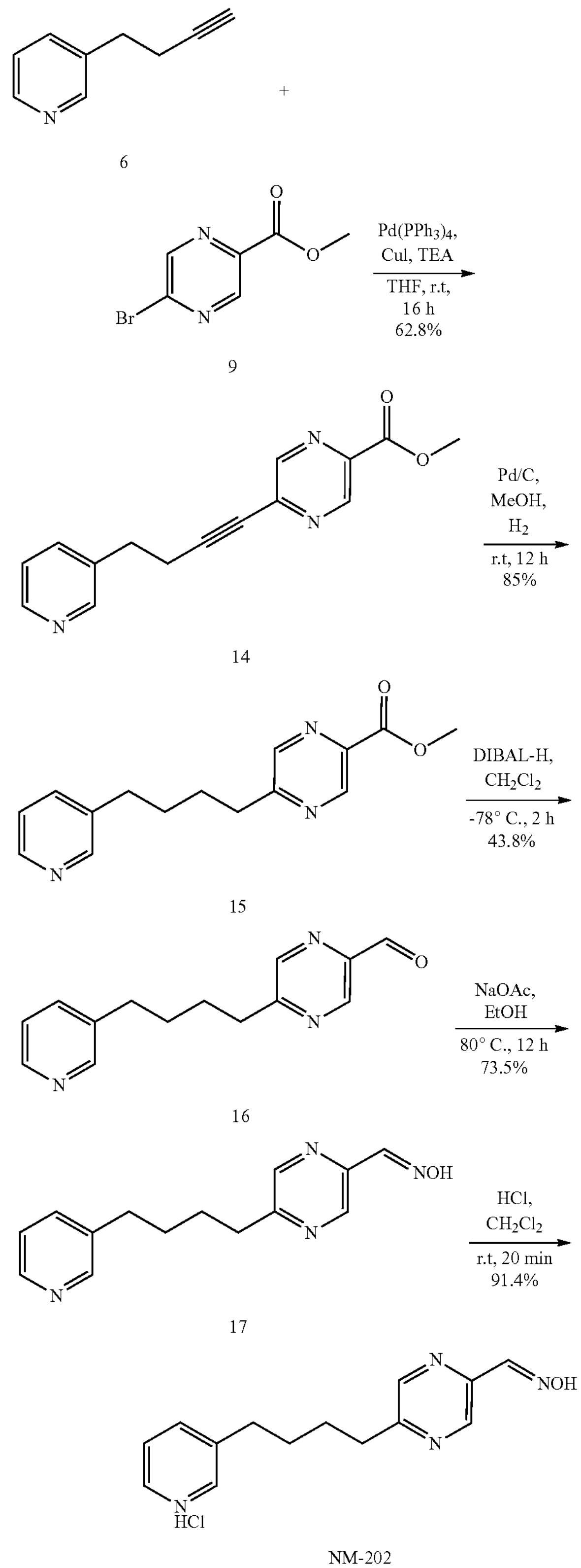

6

9

14

15

16

17

NM-202

Methyl 5-(4-(pyridin-3-yl)but-1-ynyl)pyrazine-2-carboxylate 14

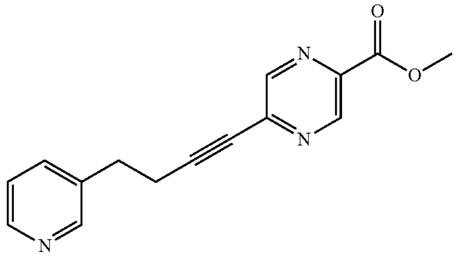

14

To a degassed solution of methyl 5-bromopyrazine-2-carboxylate 9 (364 mg, 1.677 mmol, 1.1 equiv) in THF/$Et_3N$ (12 mL/4 mL), $Pd[PPh_3]_4$ (264.8 mg, 0.2289 mmol, 0.15 equiv) and CuI (87.2 mg, 0.457 mmol, 0.3 equiv) were added. After degassing the reaction mixture for 5 min at room temperature, 3-(but-3-ynyl)pyridine 6 (200 mg, 1.526 mmol, 1 equiv) was added dropwise and the reaction mixture was stirred at the room temperature for 16 h. Upon completion, the reaction mixture was concentrated under reduced pressure and the residue was purified by column chromatography (100% EtOAc) to afford methyl 5-(4-(pyridin-3-yl)but-1-ynyl)pyrazine-2-carboxylate 14 as a pale yellow solid (250 mg, 62.8%). $R_f$ (100% EtOAc) 0.30; HRMS ($ESI^+$): m/z calcd for $C_{15}H_{14}N_3O_2^+$ 268.108053 found 268.106764; $^1$H NMR (400 MHz, $CDCl_3$): δ ppm 9.15 (d, J=1.4 Hz, 1H), 8.74-8.30 (m, 3H), 7.62 (d, J=7.8 Hz, 1H), 7.20 (s, 1H), 3.93 (s, 3H), 2.95 (t, J=7.3 Hz, 2H), 2.78 (t, J=7.1 Hz, 2H); $^{13}$C NMR (101 MHz, $CDCl_3$): δ ppm 164.08, 146.78, 145.60, 140.40, 132.14, 132.04, 131.92, 131.89, 128.54, 128.42, 97.05, 79.07, 53.18, 31.79, 21.60.

Methyl 5-(4-(pyridin-3-yl)butyl)pyrazine-2-carboxylate 15

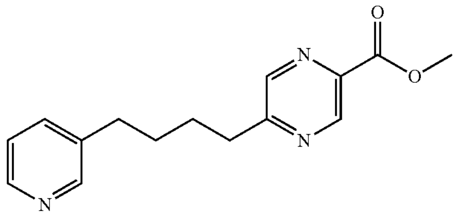

15

To a solution of methyl 5-(4-(pyridin-3-yl)but-1-ynyl) pyrazine-2-carboxylate 14 (110 mg, 0.411 mmol) in EtOAc (5 mL) was added 10% Pd/C (60 mg) at room temperature under Argon atmosphere and stirred the mixture for 12 h under $H_2$ atmosphere using balloon pressure. Upon completion, the mixture was filtered using small celite pad, concentrated under reduced pressure and purified by $SiO_2$ column chromatography (100% EtOAc) to afford Methyl 5-(4-(pyridin-3-yl)butyl)pyrazine-2-carboxylate 15 as a light brown syrup (95 mg, 85%); $R_f$ (100% EtOAc/PE) 0.2; $^1$H NMR (400 MHz, $CDCl_3$): δ ppm 9.21 (d, J=1.3 Hz, 1H), 8.54 (d, J=1.3 Hz, 1H), 8.44 (d, J=2.1 Hz, 2H), 7.47 (d, J=7.8 Hz, 1H), 7.20 (dd, J=7.7, 4.8 Hz, 1H), 3.94 (s, 3H), 2.94 (t, J=7.6 Hz, 2H), 2.66 (t, J=7.6 Hz, 2H), 1.89-1.78 (m, 2H), 1.77-1.63 (m, 2H); $^{13}C$ NMR (101 MHz, $CDCl_3$): δ ppm 164.59, 161.03, 149.81, 147.39, 145.49, 143.88, 140.72, 137.12, 135.75, 123.31, 52.98, 35.33, 32.72, 30.64, 28.53.

(E/Z)-5-(4-(pyridin-3-yl)butyl)pyrazine-2-carbaldehyde oxime 17

17

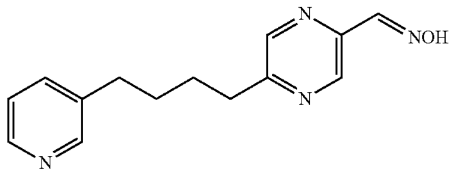

To a solution of Methyl 5-(4-(pyridin-3-yl)butyl)pyrazine-2-carboxylate (90 mg, 0331 mmol) in $CH_2Cl_2$ (4 mL) was added DIBAL-H (0.83 mL, 1M in $CH_2Cl_2$) at −78° C. and stirred over 2 h at same temperature. The mixture was quenched with MeOH (2 mL) at −78° C. and concentrated by vacuo. The white aluminum salts were removed by filtered in $CH_2Cl_2$, concentrated by vacuo and purified by column chromatography to give 5-(4-(pyridin-3-yl)butyl) pyrazine-2-carbaldehyde 16 as an off white solid (35 mg, 43%). To a solution of E-5-(4-(pyridin-3-yl)butyl)pyrazine-2-carbaldehydein EtOH (4 mL) was added hydroxylamine hydrochloride (18.4 mg, 0.187 mmol), NaOAc (32.65 mg, 0.280 mmol) and refluxed for 16 h. After concentration by vacuo, the crude product was purified by $SiO_2$ column chromatography (100% EtOAc) to afford cis-trans isomers (9:1, ratio) of (E/Z)-5-(4-(pyridin-3-yl)butyl)pyrazine-2-carbaldehyde oxime 17 as an off white solid (25 mg, 73.5%); $R_f$ 0.5%, (10% MeOH/$CH_2Cl_2$).

5-(4-(pyridin-3-yl)butyl)pyrazine-2-carbaldehyde 16

HRMS (ESI$^+$): m/z calcd for $C_{14}H_{16}N_3O^+$ 242.128789 found 242.128440; $^1H$ NMR (400 MHz, $CDCl_3$): δ 10.12 (s, 1H), 9.07 (d, J=1.2 Hz, 1H), 8.58 (d, J=1.2 Hz, 1H), 8.40 (bs, 2H), 7.48 (d, J=7.7 Hz, 1H), 7.21 (dd, J=7.6, 4.8 Hz, 1H), 2.95 (t, J=7.6 Hz, 2H), 2.68 (t, J=7.5 Hz, 2H), 1.91-1.79 (m, 2H), 1.74 (dd, J=9.4, 5.4 Hz, 2H); $^{13}C$ NMR (101 MHz, $CDCl_3$): δ 192.27, 162.02, 149.79, 147.39, 144.94, 144.37, 142.88, 137.12, 135.78, 123.36, 35.54, 32.72, 30.66, 28.51.

(E/Z)-5-(4-(pyridin-3-yl)butyl)pyrazine-2-carbaldehyde oxime 17

HRMS (ESI$^+$): m/z calcd for $C_{14}H_{17}N_4O^+$ 257.139688 found 257.140439; $^1H$ NMR (400 MHz, $CDCl_3$): δ 9.31 (d, J=1.3 Hz, 0.1H), 9.01 (d, J=1.1 Hz, 0.9H), 8.46-8.41 (m, 3H), 8.26 (s, 0.9H), 7.69 (s, 0.1H), 7.53 (d, J=7.8 Hz, 1H), 7.25 (dd, J=7.7, 4.9 Hz, 1H), 2.90 (t, J=7.6 Hz, 2H), 2.68 (t, J=7.6 Hz, 2H), 1.87-1.76 (m, 2H), 1.73-1.66 (m, 2H); $^{13}C$ NMR (101 MHz, $CDCl_3$): δ 157.55, 156.57, 149.22, 147.78, 146.86, 146.73, 145.71, 145.59, 143.41, 142.22, 141.72, 137.71, 136.52, 136.44, 123.61, 35.21, 34.83, 32.74, 30.58, 30.51, 28.71, 28.64.

(E/Z)-5-(4-(pyridin-3-yl)butyl)pyrazine-2-carbaldehyde oxime hydrochloride NM-202

NM-202

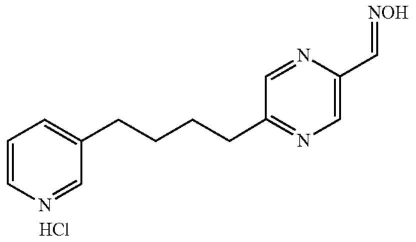

To a solution of (E)-5-(4-(pyridin-3-yl)butyl)pyrazine-2-carbaldehydeoxime 17 (18 mg, 0.065 mmol) was added 2N HCl (2 mL) at room temperature and stirred for 20 min at same temperature. Upon completion, solvent was distilled off under reduced pressure and the resulting solid was washed with diethyl ether. The solid was dried under vacuum to give cis-trans mixture (9:1 ratio) of (E/Z)-5-(4-(pyridin-3-yl)butyl)pyrazine-2-carbaldehyde oxime hydrochloride NM-202 as a light brown solid (18.8 mg, 91.4%); $^1H$ NMR (500 MHz, $CD_3OD$): δ 9.06 (s, 1H), 8.90-8.78 (m, 2H), 8.76 (d, J=5.7 Hz, 1H), 8.60 (dt, J=8.0, 1.7 Hz, 1H), 8.24 (s, 1H), 8.07 (dd, J=8.1, 5.8 Hz, 1H), 3.06 (t, J=7.4 Hz, 2H), 2.99 (t, J=7.5 Hz, 2H), 2.00-1.81 (m, 4H); $^{13}C$ NMR (126 MHz, $CD_3OD$): δ 155.02, 146.92, 146.09, 145.30, 145.01, 144.21, 143.93, 143.05, 143.01, 142.38, 142.00, 140.79, 139.08, 138.97, 138.82, 127.04, 32.96, 32.92, 32.75, 31.66, 29.49, 27.99, 27.93, 27.89.

(E)-5-(2-(pyridin-3-yl)ethyl)pyrimidine-2-carbaldehyde oxime hydrochloride NM-158

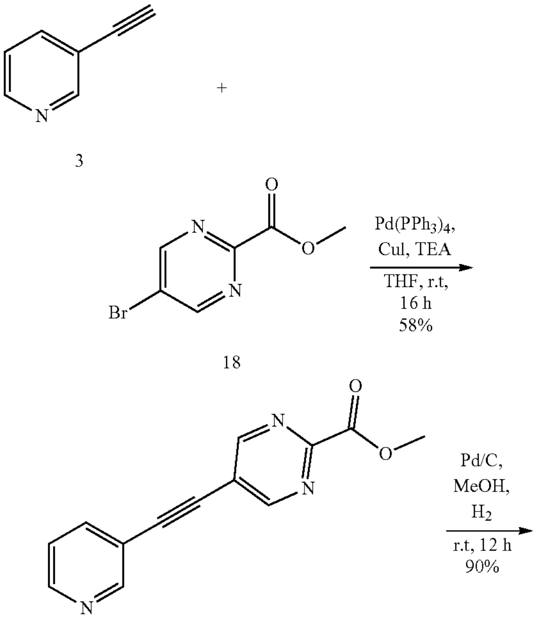

3

18

19

-continued

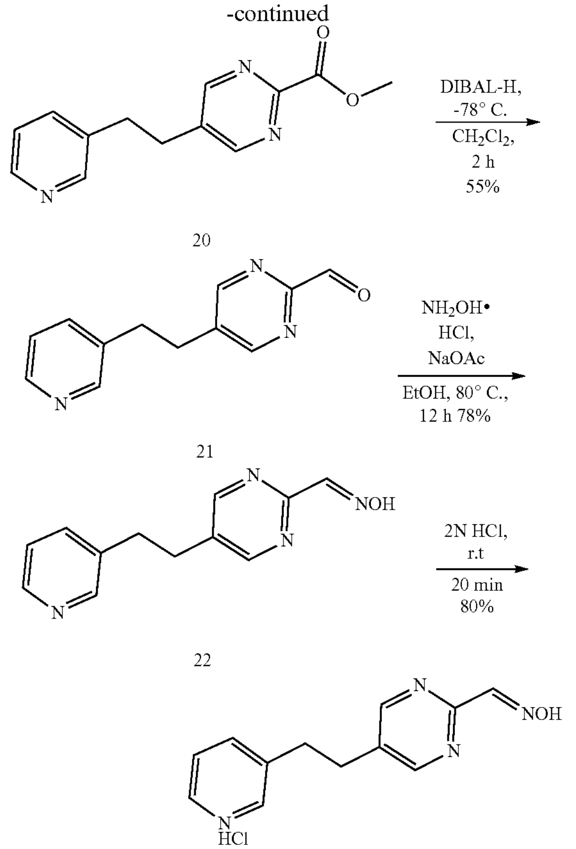

20

21

22

NM-158

Methyl 5-(pyridin-3-ylethynyl)pyrimidine-2-carboxylate 19

19

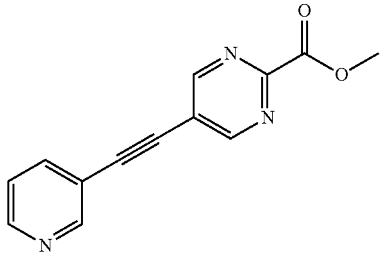

To a degassed solution of methyl 5-bromopyrimidine-2-carboxylate 18 (231.7 mg, 1.06 mmol, 1.1 equiv) in THF/$Et_3N$ (9 mL/3 mL), $Pd[PPh_3]_4$ (168.4 mg, 0.145 mmol, 0.290 equiv) and CuI (55.4 mg, 0.291 mmol, 0.3 equiv) were added. After degassing the reaction mixture for 5 min at room temperature, 3-ethynylpyridine 3 (100 mg, 1.941 mmol, 1 equiv) was added dropwise and the reaction mixture was stirred at the room temperature for 16 h. Upon completion, the reaction mixture was concentrated under reduced pressure and the residue was purified by column chromatography (EtOAc/PE, 1:1) to afford methyl 5-(pyridin-3-ylethynyl)pyrimidine-2-carboxylate 19 as a pale yellow solid (135 mg, 58%); $R_f$ (100% EtOAc) 0.3; HRMS ($ESI^+$): m/z calcd for $C_{13}H_{10}N_3O_2^+$ 240.076753 found 240.076296; $^1$H NMR (400 MHz, $CDCl_3$): δ ppm 8.98 (s, 2H), 8.77 (s, 1H), 8.59 (dd, J=5.0, 1.6 Hz, 1H), 7.81 (dt, J=7.9, 1.8 Hz, 1H), 7.30 (ddd, J=7.9, 4.9, 0.8 Hz, 1H), 4.03 (s, 3H); $^{13}$C NMR (101 MHz, $CDCl_3$): δ ppm 163.19, 159.47, 153.97, 152.47, 150.08, 138.82, 127.43, 123.28, 121.21, 118.58, 95.60, 85.03, 53.78.

Methyl 5-(2-(pyridin-3-yl)ethyl)pyrimidine-2-carboxylate 20

20

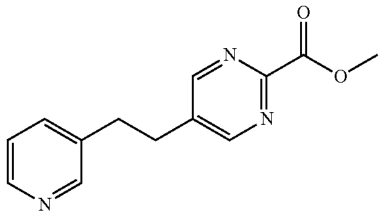

To a solution of methyl 5-(pyridin-3-ylethynyl)pyrimidine-2-carboxylate 20 (130 mg, 0.534 mmol) in MeOH (10 mL) was added 10% Pd/C (70 mg) at room temperature under Argon atmosphere and stirred the mixture for 12 h under $H_2$ atmosphere using balloon pressure. Upon completion, the mixture was filtered using small celite pad, concentrated under reduced pressure and purified by $SiO_2$ column chromatography (100% EtOAc) to afford methyl 5-(2-(pyridin-3-yl)ethyl)pyrimidine-2-carboxylate 20 as an off white solid (120 mg, 90%); $R_f$ 0.2 (100% EtOAc); HRMS ($ESI^+$): m/z calcd for $C_{13}H_{13}N_3NaO_2^+$ 266.089997 found 266.090242; $^1$H NMR (400 MHz, $CDCl_3$) δ ppm 8.71 (s, 2H), 8.50 (d, J=16.6 Hz, 2H), 7.44 (d, J=7.8 Hz, 1H), 7.26-7.20 (m, 1H), 4.09 (s, 3H), 3.11-2.96 (m, 4H); $^{13}$C NMR (101 MHz, $CDCl_3$): δ ppm 163.65, 157.65, 154.73, 149.85, 148.34, 136.05, 135.86, 53.57, 33.73, 31.84.

(E)-5-(2-(pyridin-3-yl)ethyl)pyrimidine-2-carbaldehyde oxime 22

22

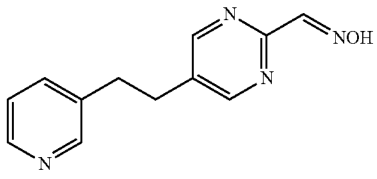

To a solution of 5-(2-(pyridin-3-yl)ethyl)pyrimidine-2-carboxylate (50 mg, 0.205 mmol) in $CH_2Cl_2$ (3 mL) was added DIBAL-H (0.51 mL, 1 M in THF) at −78° C. and stirred over 1.5 h at same temperature. The mixture was quenched with MeOH (2 mL) and concentrated by vacuo. The white aluminum salts were removed by filtered in $CH_2Cl_2$, concentrated and purified b column chromatography to give 5-(2-(pyridin-3-yl)ethyl)pyrimidine-2-carbaldehyde 21 as an off white solid. To a solution of 5-(2-(pyridin-3-yl)ethyl)pyrimidine-2-carbaldehyde (30 mg, 0219 mmols) in EtOH (5 mL) was added hydroxylamine hydrochloride (19.5 mg, 69.49 mmol), NaOAc (34.6 mg, 82.03 mmol) and then refluxed for 16 h. After concentration by vacuo, the crude product was purified by $SiO_2$ column chromatography ($MeOH/CH_2Cl_2$, 5:95) to afford (E)-5-(2-(pyridin-3-yl)ethyl)pyrimidine-2-carbaldehyde oxime 22 as an off white solid (25 mg, 78%); $R_f$ 0.5 (10% $MeOH/CH_2Cl_2$).

5-(2-(pyridin-3-yl)ethyl)pyrimidine-2-carbaldehyde 21

HRMS (ESI$^+$): m/z calcd for $C_{12}H_{11}N_3NaO^+$ 236.079433 found 236.079616; $^1H$ NMR (400 MHz, $CDCl_3$): δ 10.08 (s, 1H), 8.74 (s, 2H), 8.51-8.46 (m, 1H), 8.43 (d, J=1.5 Hz, 1H), 7.44 (dt, J=7.7, 1.8 Hz, 1H), 7.23 (dd, J=7.7, 4.7 Hz, 1H), 3.09-2.98 (m, 4H); $^{13}C$ NMR (101 MHz, $CDCl_3$): δ ppm 190.82, 158.01, 157.85, 149.80, 148.29, 136.39, 135.89, 134.64, 123.55, 33.66, 31.96.

(E)-5-(2-(pyridin-3-yl)ethyl)pyrimidine-2-carbaldehyde oxime 22

HRMS (ESI$^+$): m/z calcd for $C_{12}H_{13}N_4O^+$ 229.108387 found 229.107886; $^1H$ NMR (400 MHz, DMSO): δ 11.96 (s, 1H), 8.69 (s, 2H), 8.45-8.38 (m, 2H), 8.08 (s, 1H), 7.66 (dt, J=7.8, 1.9 Hz, 1H), 7.32 (ddd, J=7.8, 4.8, 0.6 Hz, 1H), 2.96 (s, 4H); $^{13}C$ NMR (101 MHz, DMSO): δ ppm 158.94, 157.78, 150.21, 148.26, 147.91, 136.49, 136.40, 133.71, 123.89, 33.19, 31.08.

(E)-5-(2-(pyridin-3-yl)ethyl)pyrimidine-2-carbaldehyde oxime hydrochloride NM-158

NM-158

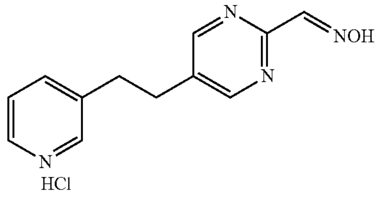

To a solution of (E)-5-(2-(pyridin-3-yl)ethyl)pyrimidine-2-carbaldehyde oxime (20 mg, 0.087 mmol) was added 2N HCl (2 mL) at room temperature and stirred for 20 min at same temperature. Upon completion, solvent was distilled off under reduced pressure and the resulting solid was washed with diethyl ether. The solid was dried under vacuum to give (E)-5-(2-(pyridin-3-yl)ethyl)pyrimidine-2-carbaldehyde oxime hydrochloride as a light yellow solid (14 mg, 80%); $R_f$ 0.4% (10% $MeOH/CH_2Cl_2$); HRMS (ESI$^+$): m/z calcd for $C_{12}H_{13}N_4O^+$ 229.108387 found 229.108821; $^1H$ NMR (400 MHz, $CD_3OD$): δ ppm 9.59-9.03 (m, 2H), 8.97 (s, 1H), 8.81 (t, J=9.2 Hz, 1H), 8.70 (t, J=11.6 Hz, 1H), 8.46 (bs, 1H), 8.11 (dt, J=15.8, 7.9 Hz, 1H), 3.44-3.32 (m, 4H); $^{13}C$ NMR (101 MHz, $CD_3OD$): δ ppm 157.61, 157.50, 147.20, 143.33, 141.21, 141.03, 139.59, 127.23, 32.17, 29.97.

Example 2: Synthesis of Compound NM-279 of the Invention (E)-6-(2-(pyridin-3-yl)ethyl)pyridazine-4-carbaldehyde oxime NM-279

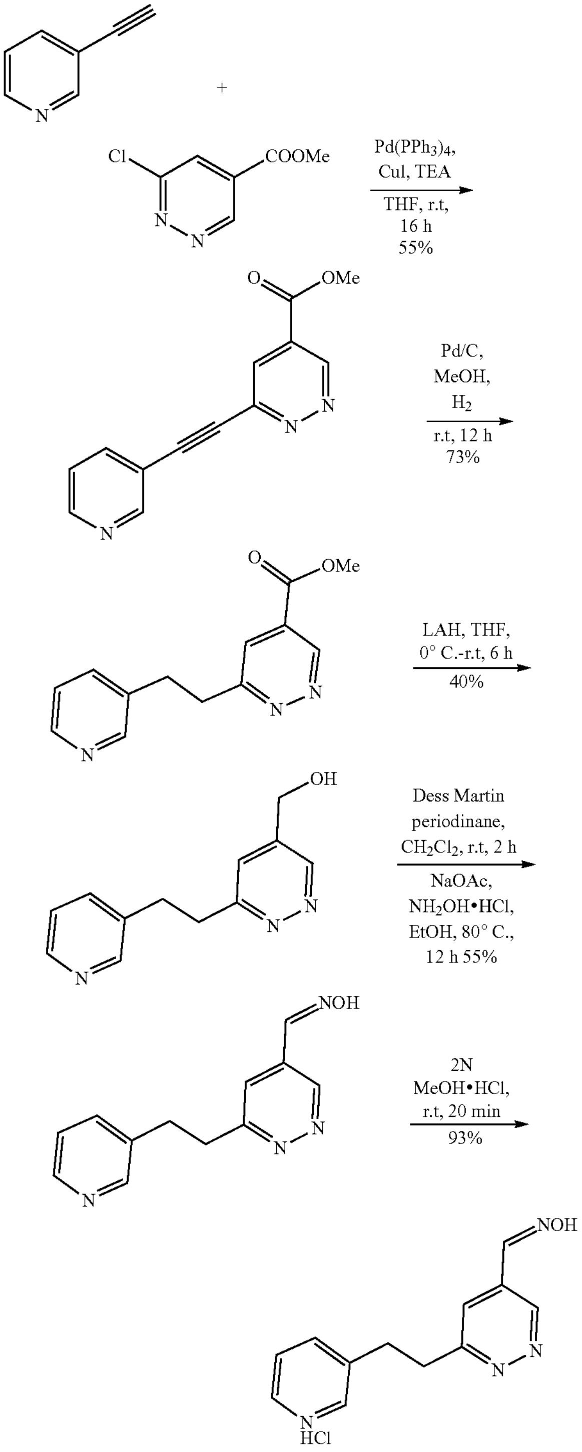

NM-279 methyl 6-(pyridin-3-ylethynyl)pyridazine-4-carboxylate

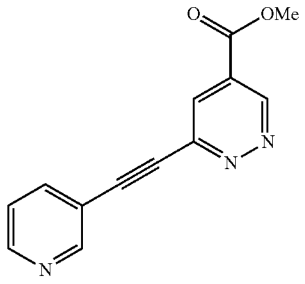 [SMILES: COC(=O)c1cnnc(C#Cc2cccnc2)c1]

To a degassed solution of methyl 6-chloropyridazine-4-carboxylate (368 mg, 2.135 mmol, 1.1 equiv) in THF/$Et_3N$ (9 mL/3 mL), Pd[$PPh_3$]$_4$ (336 mg, 0.291 mmol, 0.15 equiv) and CuI (110 mg, 0.577 mmol, 0.3 equiv) were added. After degassing the reaction mixture for 5 min at room temperature, 3-ethynylpyridine (200 mg, 1.941 mmol, 1 equiv) was added dropwise and the reaction mixture was stirred at the room temperature for 16 h. Upon completion, the reaction mixture was concentrated under reduced pressure and the residue was purified by column chromatography (EtOAc/PE, 1:1) to afford methyl 6-(pyridin-3-ylethynyl)pyridazine-4-carboxylate as a pale yellow solid (255 mg, 55%); $R_f$(50% EtOAc/PE) 0.2; HRMS (ESI$^+$): m/z calcd for $C_{13}H_{10}N_3O_2^+$ 240.076753 found 240.077901. $^1$H NMR (400 MHz, DMSO); 5 ppm 9.58 (d, J=1.7 Hz, 1H), 9.41-8.43 (m, 2H), 8.35 (d, J=1.9 Hz, 1H), 8.17 (d, J=7.8 Hz, 1H), 7.60 (s, 1H), 3.96 (s, 3H). $^{13}$C NMR (101 MHz, DMSO) δ 163.99, 152.63, 150.73, 148.30, 148.17, 139.72, 129.66, 128.10, 91.58, 88.68, 53.76.

methyl 6-(2-(pyridin-3-yl)ethyl)pyridazine-4-carboxylate

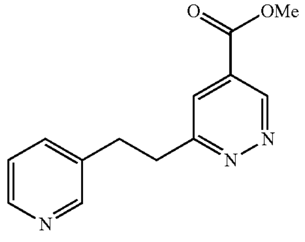 [SMILES: COC(=O)c1cnnc(CCc2cccnc2)c1]

To a solution of methyl 6-(pyridin-3-ylethynyl) pyridazine-4-carboxylate (140 mg, 0.585 mmol) in MeOH (10 mL) was added 10% Pd/C (100 mg) at room temperature under Argon atmosphere and stirred the mixture for 12 h under $H_2$ atmosphere using balloon pressure. Upon completion, the mixture was filtered using small celite pad, concentrated under reduced pressure and purified by $SiO_2$ column chromatography (EtOAc/PE, 8:2) to afford methyl 6-(2-(pyridin-3-yl)ethyl)pyridazine-4-carboxylate as light brown syrup (105 mg, 73%); $R_f$(100% EtOAc) 0.3; HRMS (ESI$^+$): m/z calcd for $C_{13}H_{14}N_3O_2^+$ 244.108053 found 244.107786; $^1$H NMR (400 MHz, $CDCl_3$): δ 9.52 (d, J=2.0 Hz, 1H), 8.47 (bs, 2H), 7.76 (d, J=2.0 Hz, 1H), 7.56 (dt, J=7.7, 1.8 Hz, 1H), 7.23 (dd, J=7.7, 4.8 Hz, 1H), 4.00 (s, 3H), 3.40 (dd, J=9.1, 6.6 Hz, 2H), 3.21 (dd, J=9.1, 6.7 Hz, 2H). $^{13}$C NMR (101 MHz, $CDCl_3$): δ 164.29, 162.97, 149.60, 147.92, 147.67, 136.22, 135.82, 127.91, 125.61, 123.57, 53.17, 37.49, 32.28.

(6-(2-(pyridin-3-yl)ethyl)pyridazin-4-yl)methanol

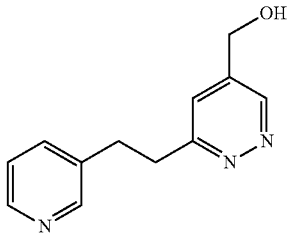 [SMILES: OCc1cnnc(CCc2cccnc2)c1]

To a solution of $LiAlH_4$ (19.5 mg, 0.513 mmol) in THF (3 mL) at 0° C. was added methyl 6-(2-(pyridin-3-yl)ethyl) pyridazine-4-carboxylate (50 mg, 0.205 mmol) in THF (2 mL) dropwise and stirred for 6 h at room temperature. Upon completion, the mixture was quenched with Fisher method and filtered the white aluminum salts. The filtrates were concentrated and purified by $SiO_2$ column chromatography (100% EtOAc) to give (6-(2-(pyridin-3-yl)ethyl)pyridazin-4-yl)methanol as a light brown colour solid (18 mg, 40%); $R_f$0.3 (10% MeOH in $CH_2Cl_2$); HRMS (ESI$^+$): m/z calcd for $C_{12}H_{14}N_3O^+$ 216.113139 found 216.11268. $^1$H NMR (400 MHz, $CDCl_3$) δ 9.04 (d, J=1.9 Hz, 1H), 8.53-8.37 (m, 2H), 7.64 (d, J=7.8 Hz, 1H), 7.35-7.32 (m, 1H), 7.32-7.26 (m, 1H), 4.78 (s, 2H), 3.37-3.28 (m, 2H), 3.25-3.16 (m, 2H).

(E)-6-(2-(pyridin-3-yl)ethyl)pyridazine-4-carbaldehyde oxime

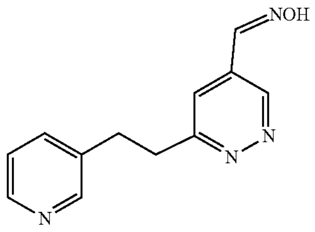

To a solution of (6-(2-(pyridin-3-yl)ethyl)pyridazin-4-yl) methanol (18 mg, 0.083 mmol) in $CH_2Cl_2$ (3 mL) was added dess-matin periodinane (42.5 mg, 0.100 mmols) and $NaHCO_3$ (18.7 mg, 0.222 mmols) at 0° C. and stirred for 2 h. Upon completion, filtered the mixture on small celite pad and concentrated. The crude was used in the next reaction without further purification. To a solution of 6-(2-(pyridin-3-yl)ethyl)pyridazine-4-carbaldehyde (18 mg, 0.084 mmol) in EtOH (4 mL) was added hydroxylamine hydrochloride (11.7 mg, 0.168 mmol), NaOAc (26.8 mg, 0.125 mmol) and refluxed for 16 h. After concentration by vacuo, the crude product was purified by $SiO_2$ column chromatography (100% EtOAc) to afford 8:2 ratio of (E/Z)-6-(2-(pyridin-3-yl)ethyl)pyridazine-4-carbaldehyde oxime as an off white solid (10.5 mg, 55% for two steps); $R_f$0.5%, (10% MeOH/$CH_2Cl_2$); $^1$H NMR (400 MHz, $CD_3OD$) δ 9.48 (d, J=1.9 Hz, 0.2H), 9.26 (d, J=1.9 Hz, 1H), 8.52-8.28 (m, 2.4H), 8.11 (s, 1H), 7.99 (dd, J=7.9, 1.0 Hz, 0.2H), 7.80-7.76 (m, 1.2H), 7.71 (d, J=2.0 Hz, 1H), 7.47 (s, 0.2H), 7.39 (dd, J=7.7, 4.9

Hz, 1.2H), 3.38-3.30 (m, 2H), 3.23-3.16 (m, 2H). $^{13}C$ NMR (101 MHz, $CD_3OD$) δ 163.16, 162.85, 149.03, 148.54, 146.44, 146.34, 143.76, 140.69, 140.14, 137.39, 137.07, 133.19, 131.67, 129.83, 128.95, 127.62, 127.05, 123.95, 36.62, 36.49, 31.85, 31.79.

(E)-6-(2-(pyridin-3-yl)ethyl)pyridazine-4-carbaldehyde oxime hydrochloride NM-279

NM-279

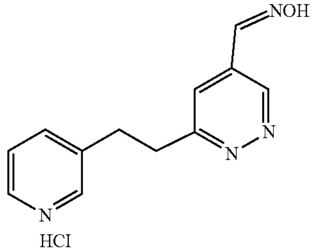

To a solution of (E)-6-(2-(pyridin-3-yl)ethyl)pyridazine-4-carbaldehyde oxime (5 mg, 0.087 mmol) was added 2N MeOH·HCl (2 mL) at room temperature and stirred for 20 min at same temperature. Upon completion, solvent was distilled off under reduced pressure and the resulting solid was washed with diethyl ether (2×3 mL). The solid was dried under vacuum to give (E)-6-(2-(pyridin-3-yl)ethyl) pyridazine-4-carbaldehyde oxime hydrochloride NM-279 as a light yellow solid (5.4 mg, 93% yield); $^{1}H$ NMR (400 MHz, $CD_3OD$): δ 9.70 (s, 1H), 8.98 (s, 1H), 8.83 (d, J=5.5 Hz, 1H), 8.72 (d, J=8.1 Hz, 1H), 8.61 (d, J=1.0 Hz, 1H), 8.37 (s, 1H), 8.13 (dd, J=8.0, 5.8 Hz, 1H), 3.70-3.58 (m, 2H), 3.54-3.46 (m, 2H). $^{1}3C$ NMR (101 MHz, $CD_3OD$): δ 147.13, 142.52, 141.31, 140.91, 140.41, 139.78, 132.06, 130.55, 130.16, 127.66, 127.26, 33.44, 29.96.

Example 3: Synthesis of Compound NM-251 of the Invention

(E)-5-(4-(pyridin-3-yl)butyl)pyrimidine-2-carbaldehyde oxime hydrochloride NM-251

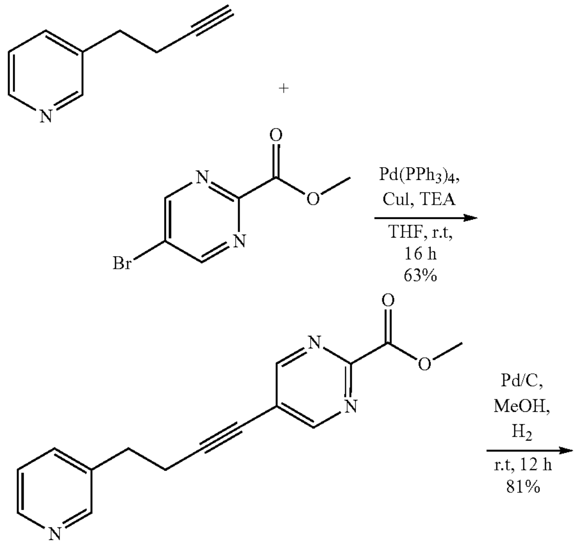

-continued

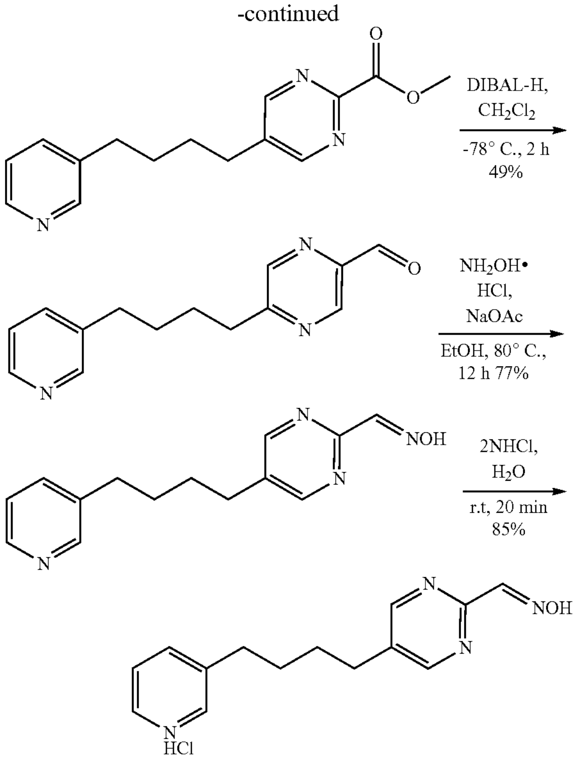

methyl 5-(4-(pyridin-3-yl)but-1-yn-1-yl)pyrimidine-2-carboxylate

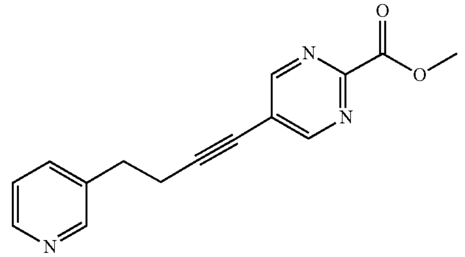 [SMILES: COC(=O)c1ncc(C#CCCc2cccnc2)cn1]

To a degassed solution of methyl 5-bromopyrimidine-2-carboxylate (200 mg, 0.921 mmol, 1.1 equiv) in THF/$Et_3N$ (12 mL/4 mL), Pd[$PPh_3$]$_4$ (213 mg, 0.184 mmol, 0.2 equiv) and CuI (70.2 mg, 0.368 mmol, 0.4 equiv) were added. After degassing the reaction mixture for 5 min at room temperature, 3-(but-3-ynyl)pyridine 6 (144 mg, 1.099 mmol, 1.2 equiv) was added dropwise and the reaction mixture was stirred at the room temperature for 16 h. Upon completion, the reaction mixture was concentrated under reduced pressure and the residue was purified by column chromatography (EtOAc) to afford methyl 5-(4-(pyridin-3-yl)but-1-yn-1-yl)pyrimidine-2-carboxylate as a pale yellow solid (156 mg, 63%). $R_f$ (50% EtOAc) 0.25; HRMS (ESI$^+$): m/z calcd for $C_{15}H_{14}N_3O_2^+$ 268.108053 found 268.109550; $^{1}H$ NMR (400 MHz, $CDCl_3$): δ 8.84 (s, 2H), 8.58 (bs, 2H), 7.63 (d, J=7.8 Hz, 1H), 7.35-7.28 (m, 1H), 4.08 (s, 3H), 2.99 (t, J=7.2 Hz, 2H), 2.84 (t, J=7.2 Hz, 2H). $^{13}C$ NMR (101 MHz, $CDCl_3$): δ 163.27, 159.44, 153.39, 149.66, 147.99, 136.14, 121.97, 99.38, 75.20, 53.66, 31.54, 21.49.

methyl 5-(4-(pyridin-3-yl)butyl)pyrimidine-2-carboxylate

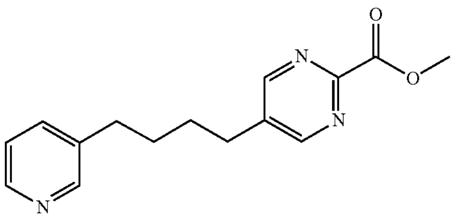 [SMILES: COC(=O)c1ncc(CCCCc2cccnc2)cn1]

To a solution of methyl 5-(4-(pyridin-3-yl)but-1-yn-1-yl)pyrimidine-2-carboxylate (100 mg, 0.374 mmol) in MeOH (5 mL) was added 10% Pd/C (50 mg) at room temperature under Argon atmosphere and stirred the mixture for 12 h under $H_2$ atmosphere using balloon pressure. Upon completion, the mixture was filtered using small celite pad, concentrated under reduced pressure and purified by $SiO_2$ column chromatography (100% EtOAc) to afford methyl 5-(4-(pyridin-3-yl)butyl)pyrimidine-2-carboxylate as a light brown syrup (95 mg, 81% yield); $R_f$ 0.2 (100% EtOAc); HRMS (ESI$^+$): m/z calcd for $C_{15}H_{18}N_3O_2^+$ 272.135393 found 272.138198; $^1$H NMR (400 MHz, $CDCl_3$): δ 8.71 (s, 2H), 8.41 (bs, 2H), 7.44 (dt, J=7.7, 1.8 Hz, 1H), 7.18 (dd, J=7.7, 4.8 Hz, 1H), 4.03 (s, 3H), 2.75-2.67 (m, 2H), 2.67-2.59 (m, 2H), 1.76-1.63 (m, 4H). $^{13}$C NMR (101 MHz, $CDCl_3$): δ 163.73, 157.45, 154.43, 149.70, 147.46, 137.42, 136.85, 135.72, 123.38, 53.46, 32.60, 30.48, 30.20, 29.95, 29.64.

(E)-5-(4-(pyridin-3-yl)butyl)pyrimidine-2-carbaldehyde oxime

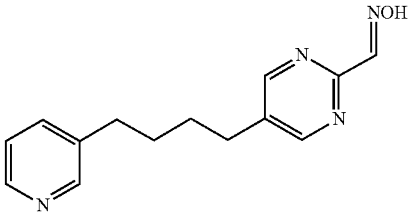

To a solution of methyl 5-(4-(pyridin-3-yl)butyl)pyrimidine-2-carboxylate (60 mg, 0331 mmol) in $CH_2Cl_2$ (4 mL) was added DIBAL-H (0.55 mL, 1M in $CH_2Cl_2$) at −78° C. and stirred over 2 hours at same temperature. The mixture was quenched with MeOH (2 mL) at −78° C. and concentrated by vacuo. The white aluminum salts were removed by filtered in $CH_2Cl_2$, concentrated by vacuo and purified by preparative TLC to give 5-(4-(pyridin-3-yl)butyl)pyrimidine-2-carbaldehyde as an off white solid (26 mg, 49%). To a solution of 5-(4-(pyridin-3-yl)butyl)pyrimidine-2-carbaldehyde (22 mg, 0.091 mmol) in EtOH (4 mL) was added hydroxylamine hydrochloride (12.6 mg, 0.182 mmol), NaOAc (29 mg, 0.273 mmol) and refluxed for 12 h. After concentration by vacuo, the crude product was purified by $SiO_2$ column chromatography (100% EtOAc) to afford (E)-5-(4-(pyridin-3-yl)butyl)pyrimidine-2-carbaldehyde oxime as an off white solid (18 mg, 77%); $R_f$ 0.5%, (10% MeOH/$CH_2Cl_2$).

5-(4-(pyridin-3-yl)butyl)pyrimidine-2-carbaldehyde: HRMS (ESI$^+$): m/z calcd for $C_{14}H_{15}N_3NaO^+$ 264.110733 found 264.109622; $^1$H NMR (400 MHz, $CDCl_3$): δ 10.09 (d, J=6.8 Hz, 1H), 8.79 (s, 2H), 8.46 (bs, 2H), 7.49 (d, J=7.8 Hz, 1H), 7.24 (dd, J=7.7, 4.8 Hz, 1H), 2.77 (t, J=6.9 Hz, 2H), 2.68 (t, J=6.9 Hz, 2H), 1.78-1.68 (m, 4H). $^{13}$C NMR (101 MHz, $CDCl_3$): δ 190.93, 157.89, 157.68, 157.48, 156.96, 149.59, 147.38, 137.78, 136.94, 135.92, 123.48, 32.64, 30.53, 30.42, 29.95, 29.68.

(E)-5-(4-(pyridin-3-yl)butyl)pyrimidine-2-carbaldehyde oxime: HRMS (ESI$^+$): m/z calcd for $C_{14}H_{17}N_4O^+$ 257.139688 found 257.138953; $^1$H NMR (400 MHz, $CD_3OD$): δ 8.93-8.51 (m, 2H), 8.50-8.30 (m, 2H), 8.04 (bs, 1H), 7.72 (d, J=7.8 Hz, 1H), 7.37 (dd, J=7.7, 4.8 Hz, 1H), 2.86-2.36 (m, 4H), 1.82-1.59 (m, 4H). $^{13}$C NMR (126 MHz, $CD_3OD$): δ 157.05, 148.59, 146.14, 138.47, 136.85, 123.81, 32.00, 30.29, 29.78, 29.35.

(E)-5-(4-(pyridin-3-yl)butyl)pyrimidine-2-carbaldehyde oxime hydrochloride NM-251

NM-251

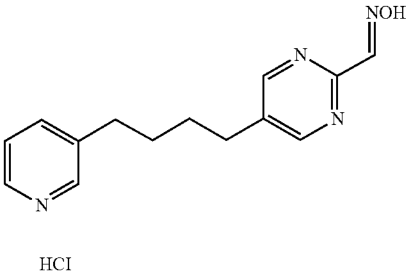

To a solution of (E)-5-(4-(pyridin-3-yl)butyl)pyrimidine-2-carbaldehyde oxime (15 mg, 0.058 mmol) was added aq.2N HCl (2 mL) at room temperature and stirred for 20 min at same temperature. Upon completion, solvent was distilled off under reduced pressure and the resulting solid was washed with diethyl ether. The solid was dried under vacuum to give cis-trans mixture of (E)-5-(4-(pyridin-3-yl)butyl)pyrimidine-2-carbaldehyde oxime hydrochloride NM-251 as an off white solid (14.6 mg, 85%); $^1$H NMR (400 MHz, $CD_3OD$): δ 9.89-8.20 (m, 6H), 8.07 (dd, J=8.0, 5.8 Hz, 1H), 3.12-2.74 (m, 4H), 1.95-1.71 (m, 4H). $^{13}$C NMR (101 MHz, $CD_3OD$): δ 156.94, 146.88, 143.07, 140.78, 138.98, 127.02, 31.69, 29.51, 29.40, 29.23.

Example 4: synthesis of (Z/E)-6-((1-methyl-1H-imidazol-5-yl)ethynyl)pyridazine-3-carbaldehyde oxime FR-156

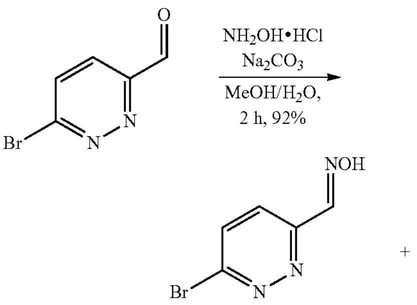

FR-155

-continued

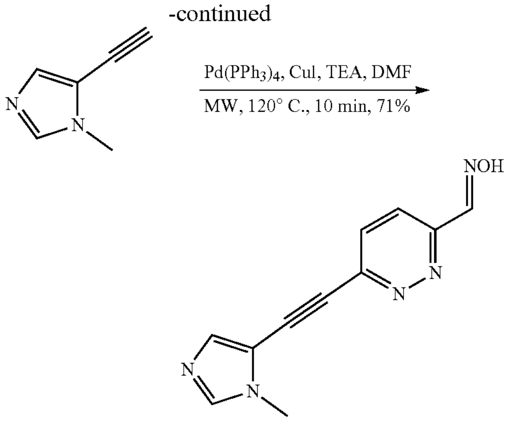

FR-156

(Z/E)-6-bromopyridazine-3-carbaldehyde oxime FR-155

FR-155

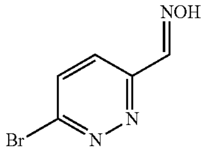

A solution of commercially available 6-bromopyridazine-3-carbaldehyde (100 mg, 0.534 mmol, 1 equiv), hydroxylamine hydrochloride (55.74 mg, 0.802 mmol, 1.5 equiv), and $Na_2CO_3$ (170 mg, 1.60 mmol, 3 equiv) in 1:1 ratio of $MeOH/H_2O$ (10 mL) was stirred at room temperature for 2 h. After completion (checked by TLC), MeOH was distilled off under reduced pressure and extracted with EtOAc (10 mL×3), washed with brine (10 mL) and water (10 mL). The organic layers dried over anhydrous $Na_2SO_4$ and distilled under reduced pressure, and the residue was purified by column chromatography (EtOAc/PE 30:70) to afford the (Z/E)-6-bromopyridazine-3-carbaldehyde oxime as an off white solid (100 mg, 92%); $R_f$ (30% EtOAc/PE) 0.3; $^1$H NMR (400 MHz, Methanol-$d_4$) δ 7.88 (d, J=8.8 Hz, 1H), 7.67 (d, J=8.9 Hz, 1H), 5.61 (s, 1H); $^{13}$C NMR (101 MHz, Methanol-$d_4$): δ ppm 155.41, 150.47, 145.63, 130.52, 126.92.

(Z/E)-6-((1-methyl-1H-imidazol-5-yl)ethynyl) pyridazine-3-carbaldehyde oxime FR-156

FR-156

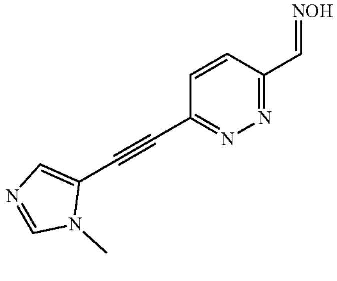

To a degassed solution of (Z/E)-6-bromopyridazine-3-carbaldehyde oxime FR-155 (50 mg, 0.247 mmol, 1 equiv) in $DMF/Et_3N$ (8 mL/2 mL), $Pd[PPh_3]_4$ (14.3 mg, 0.012 mmol, 0.05 equiv) and CuI (2.36 mg, 0.012 mmol, 0.05 equiv) were added. After degassing the reaction mixture for 5 min at room temperature, the alkyne (5-ethynyl-1-methyl-1H-imidazole, 28.89 mg, 0.272 mmol, 1.1 equiv) was added dropwise and the reaction mixture was subjected to microwave irradiation for 10 min at 120° C. After completion (monitored by TLC), the reaction mixture was concentrated under reduced pressure and the residue was purified by column chromatography (MeOH/EtOAc, 6%) to afford the desired coupled (Z/E)-6-((1-methyl-1H-imidazol-5-yl)ethynyl)pyridazine-3-carbaldehyde oxime FR-156 as a yellow solid (40 mg, 71%). $R_f$ (pure EA) 0.25; $^1$H NMR (400 MHz, Acetic Acid-$d_4$) δ 8.65 (d, J=6.6 Hz, 2H), 8.28 (d, J=8.9 Hz, 1H), 8.04 (dd, J=8.8, 0.6 Hz, 1H), 7.95 (s, 1H), 4.09 (s, 3H). $^{13}$C NMR (101 MHz, Acetic Acid-$d_4$) δ 154.18, 146.53, 146.22, 138.66, 131.02, 129.59, 124.18, 115.83, 92.92, 80.43, 33.21.

Example 5: In Vitro Reactivation of Human Acetylcholinesterase (hAChE) by Compounds of the Invention Compounds NM-45, NM-65, NM-118, NM-158 were tested for their reactivation properties of hAChE inhibited by O-ethyl S-[2-(diisopropylamino)ethyl] methylphosphonothioate (VX), tabun, sarin or paraoxon.

2-PAM (pralidoxime or 2-[(E)-(hydroxyimino)methyl]-1-methylpyridinium) and $H_{16}$ (asoxime chloride or [1-[(4-carbamoylpyridin-1-ium-1-yl)methoxymethyl]pyridin-2-ylidene]methyl-oxoazanium dichloride) were used as comparative compounds.

Inhibition of hAChE by OPNAs. Recombinant hAChE was produced and purified as previously described (see reference https://www.ncbi.nlm.nih.gov/pubmed/31132435). VX, sarin and tabun have been supplied by DGA maitrise NRBC (Vert le Petit, France).

Stock solutions of OPNA at 5 mM in isopropanol were used to inhibit the purified hAChE as previously described [Carletti, E. et al. 2008]. Briefly, a ten-fold excess of OPNA was used to perform the inhibition of hAChE in a sodium phosphate buffer (100 mM, pH 7.4, 0.1% BSA) at 25° C. Complete inhibition of hAChE was monitored by measuring the residual activity with a modified Ellman assay as previously described [Ellman, G. L., et al. 1961] and excess of OPNA were removed by using a desalting PD-10 column (GE Healthcare).

$IC_{50}$ measurements. Compounds were dissolved in water to make 40 mM stock solutions. Recombinant hAChE activity was measured spectrophotometrically at 25° C., monitoring the absorbance at 412 nm, in 1 mL of Ellman's buffer (0.5 mM DTNB, 0.1% BSA, 0.1 M phosphate, pH 7.4), in the presence of appropriate oxime concentrations. Measurements were performed at least in duplicate for each concentration tested. The oxime concentration producing 50% inhibition was determined by nonlinear fitting with ProFit (Quantumsoft) using the standard IC 50 equation: % activity=100×IC50/(IC50+[Ox]).

Reactivation of hAChE inhibited by OPNAs. The ability of the compounds to reactivate OP-inhibited hAChE were assessed with a modified Ellman assay using a microplate reader (SPARK 10M, Tecan) and a continuous method described previously [Kitz, R. J., et al. 1965, Worek, F., et al., 2004] with minor modifications. Briefly, the desired oximes concentrations to be tested were dispensed in a 96-well flat-bottomed polystyrene microplate containing 0.1% BSA phosphate buffer and DTNB. At t=0, OP-inhibited hAChE and acetylthiocholine (ATCh) diluted in 0.1% BSA phosphate buffer were injected in each well containing oximes using the built-in injectors of the microplate reader to a final volume of 200 µL. ATCh hydrolysis was continuously monitored over 30 minutes and the increase of absorbance at 412 nm recorded every 10 seconds at 25° C. Activities were individually corrected for oxime-induced hydrolysis of ATCh.

Reactivation of OP-inhibited hAChE by oximes proceeds according to scheme 1 and kinetics of oximes reactivation were determined as previously described [Worek, F., et al., 2004]. For each oxime concentration, the apparent reactivation rate, $k_{obs}$, the dissociation constant, $K_D$ and the reactivation rate constant, $k_r$, were calculated by nonlinear fitting with ProFit (Quantumsoft) using the standard oxime-concentration-dependent reactivation equation (1):

Scheme 1

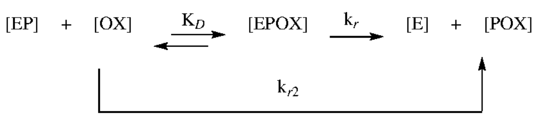

$$k_{obs} = \frac{k_r[OX]}{K_D + [OX]} \quad \text{Eq (1)}$$

When $[OX] \ll K_D$, Eq (1) simplifies to Eq (2):

$$k_{obs} = \left(\frac{k_r}{K_D}\right)[OX] \quad \text{Eq (2)}$$

The second order reactivation rate constant $k_{r2}$, describing the specific reactivity can be derived from Eq (2).

$$k_{r2} = \frac{k_r}{K_D} \quad \text{Eq (3)}$$

For the continuous method of recording OP-inhibited hAChE reactivation by oximes, the velocity of substrate hydrolysis (v) is proportional to the concentration of the reactivated hAChE and is expressed and derived as equation 4 and 5 respectively. $v_t$ is the velocity at time t and $v_0$ represents the maximum velocity. Equation 5 was used to determine the $k_{obs}$ by non-linear regression analysis for each individual oxime concentration with ProFit (Quantumsoft).

$$v_t = v_0\left(1 - e^{-k_{obs}^t}\right) \quad \text{Eq (4)}$$

$$-d[S] = \int_0^t v dt = v_0 t + \frac{v_0}{k_{obs}}\left(e^{-k_{obs}^t} - 1\right) \quad \text{Eq (5)}$$

The results are as follows:

TABLE 1

Reactivation of OP-inhibited human hAChE by oximes 2-PAM, HI-6 and NMs

| OP | Oximes | $k_r$ (min$^{-1}$) | $K_D$ (µM) | $k_{r2}$ (mM$^{-1}$ · min$^{-1}$) |
|---|---|---|---|---|
| VX | 2-PAM | 0.2 ± 0.01 | 26 ± 7 | 7 |
| | HI-6 | 0.4 ± 0.02 | 19 ± 4 | 20 |
| | NM45 | 0 | 0 | 0 |
| | NM65 | 0.1 ± 0.002 | 4 ± 0.5 | 25 |
| | NM118 | 0.1 ± 0.001 | 3 ± 0.3 | 33 |
| | NM158 | 0.2 ± 0.001 | 145 ± 20 | 1.4 |
| Sarin | 2-PAM | 0.3 ± 0.02 | 25 ± 7 | 11 |
| | HI-6 | 0.8 ± 0.06 | 57 ± 11 | 13 |
| | NM45 | 0 | 0 | 0 |
| | NM65 | 0.1 ± 0.003 | 7 ± 2 | 14 |
| | NM118 | 0.09 ± 0.001 | 6 ± 0.5 | 15 |
| | NM158 | 0.1 ± 0.002 | 11 ± 1 | 8 |
| Tabun | 2-PAM | 0.5 ± 0.2 | 211 ± 113 | 2 |
| | HI-6 | 0 | 0 | 0 |
| | NM45 | 0 | 0 | 0 |
| | NM65 | 0 | 0 | 0 |
| | NM118 | 0 | 0 | 0 |
| | NM158 | 0 | 0 | 0 |
| Paraoxon | 2-PAM | 0.07 ± 0.02 | 68 ± 16 | 1 |
| | HI-6 | 0.8 ± 0.06 | 290 ± 70 | 0.4 |
| | NM45 | 0 | 0 | 0 |
| | NM65 | 0.2 ± 0.004 | 1.3 ± 0.2 | 153 |
| | NM118 | 0.2 ± 0.01 | 58 ± 11 | 3.5 |
| | NM158 | 0.06 ± 0.002 | 106 ± 9 | 0.6 |

TABLE 2

Reactivation of OP-inhibited human hAChE by oximes 2-PAM, HI-6 and NMs

| Oxime | IC50 (µM) |
|---|---|
| 2-PAM | 580 ± 28 |
| HI-6 | 82 ± 6 |
| NM45 | 57 ± 12 |
| NM65 | 36 ± 6 |
| NM118 | 459 ± 22 |
| NM158 | 851 ± 76 |

These results show that the compounds of the invention have a broad spectrum of reactivation of OPNA-inhibited AChE: particularly they show an increased efficacy for VX and paraoxon, and a good potency against sarin.

Example 6: Transport Experiments Across the In Vitro Human Blood-Brain Barrier (BBB) Model for Compound NM-65

1. Design of the Human In Vitro BBB Model:

The in vitro human BBB model was set up as previously described by Cecchelli et al. (R. Cecchelli, S. Aday, E. Sevin, C. Almeida, M. Culot, L. Dehouck, C. Coisne, B. Engelhardt, M. P. Dehouck, L. Ferreira, PLoS One 2014, 9). Briefly, CD34+ endothelial cells, isolated from human umbilical cord blood as previously described by Pedroso et al. (C. Pedroso, A. Tellechea, L. Moura, I. Fidalgo-Carvalho, J. Duarte, E. Carvalho, L. Ferreira, PLoS One 2011, 6) were plated on 0.2% (w/v) gelatin-coated 100 mm Petri dish in ECM basal medium (ScienCell Research laboratories, Carlsbad, CA, USA) supplemented with 5% FBS, 1% endothelial cell growth supplement (ScienCell Research laboratories) and 50 µg/mL gentamycin (Biochrom AG, Berlin, Germany). In parallel, bovine pericytes were seeded on 0.2% (w/v) gelatin-coated 100 mm Petri dish and cultured in Dulbecco's Modified Eagle's Medium (DMEM) (Sigma-Aldrich, Saint-Quentin Fallavier, France) supplemented with 20% FBS, 2 mM L-glutamine and 50 µg/mL gentamycin. After two days of culture, both cell types reached confluence and got trypsinized. 50 000 pericytes were seeded into gelatin-coated wells from 12-well plates (Corning, The Netherlands) whereas CD34+ endothelial cells were plated onto matrigel-coated filter inserts (Transwell® Costar inserts, 0.4 µm pore size; Corning) at the cell density of 80 000 cells/insert and placed on top of pericyte containing wells in ECM basal medium supplemented with 5% FBS, 1% endothelial cell growth supplement (ScienCell Research laboratories) and 50 µg/mL gentamycin.

2. BBB Permeability Assay of Oximes and Control Molecules:

Upon 6 days of coculture, CD34+ endothelial cells form confluent cell monolayers that fully display brain-like endothelial cell (BLECs) properties with a proper BBB phenotype (Cecchelli et al., 2014). These cells grown on inserts were transferred to 12-well plates containing 1.5 mL per well (abluminal compartment) of HEPES buffered-Ringer's solution (RH; 150 mM NaCl, 5.2 mM KCl, 2.2 mM NaCl2, 0.2 mM MgCl2, 6 mM NaHCO3, 2.8 mM S28 glucose, 5 mM HEPES. Medium in apical chambers (luminal compartment) was removed and replaced by 0.5 mL of RH containing Lucifer Yellow (0.45 kDa, 25 µM) and either NM-65, 2-PAM, HI-6 or obidoxime. All oximes were dissolved in pure DMSO and tested at 50 µM in RH (DMSO 0.125% at final concentration) for a diffusion duration of an hour. Radiolabeled 3H-diazepam and 3H-atazanavir were used as control molecules because their transport through the BBB is well known. At different time points, inserts were moved to other wells containing 1.5 mL of RH, to avoid any flux of compounds from the abluminal to the luminal compartments. Incubations were performed at 37° C. in 5% CO2. Afterwards, the fluorescence of the diffused Lucifer Yellow was quantified using a synergy H1 multiplate reader (Biotek, Colmar, France) with the excitation/emission wavelength setting 432 nm/538 nm. Quantification of radiolabeled 3H-atazanavir (Hartmann Analytic, Germany) and 3H-diazepam (Biotrend, Germany) was performed using a scintillation counter TriCarb 2100TR (PerkinElmer, USA). The amount of each diffused oxime in the abluminal compartment was measured by mass spectrometry with a TripleTOF 5600+ System (AB SCIEX, Concord, ON, Canada).

3. Quantification of Oximes by LC-MS/MS:

Quantification of compounds NM-65, 2-PAM, HI-6, obidoxime, diazepam and atazanavir, was performed using AB SCIEX TripleTOF® 5600 mass spectrometer (ABSciex, Singapore) coupled with an Ekspert™ nanoLC 400 System. For all compounds, the mobile phases were water with 0.1% formic acid (mobile phase A) and acetonitrile with 0.1% formic acid (mobile phase B). The flow rate was 20 uL/min and the volume of injection was 5 uL. Separations were carried out on an Eksigent 3Phenyl-120 column (0.5×50 mm, particle size 3 µm). Temperatures were 8° C. for the autosampler and 35° C. for columns.

4. Results for NM-65 Compared to Standard Antidotes and Controls:

The endothelial permeability coefficients (Pe, expressed in $cm \cdot min^{-1}$+/−SD) of new reactivator NM-65, compared with current aldoximes 2-PAM, HI-6 and obidoxime, as well as to diazepam and atazanavir, were measured. Pe values were measured in the human in vitro BBB model at 50 µm. Data were analysed by using GraphPad Prism software.

The Pe value of the current aldoxime, 2-PAM ($Pe_{2\text{-}PAM}=2.9\times10^{-3}$ $cm \cdot min^{-1}$), was not significantly different from the Pe of atazanavir ($P_{eatazanavir}=1.1\times10^{-3}$ $cm \cdot min^{-1}$) known to cross the BBB relatively slowly. The Pe values of obidoxime ($Pe_{obidoxime}=0.7\times10^{3}$ $cm \cdot min^{-1}$) and HI-6 ($Pe_{Hi\text{-}6}=0.2\times10^{-3}$ $cm \cdot min^{-1}$) were lower than that of 2-PAM. The Pe values of 2-PAM and diazepam presented a significant difference. Diazepam ($Pe_{diazepam}=8.1\times0\text{-}3$ $cm \cdot min^{-1}$) is usually described to cross the BBB rapidly.

The diffusion of NM-65 ($Pe_{NM65}=5.4\times10^{-3}$ $cm \cdot min^{-1}$) across the hBLEC monolayer was higher than the BBB permeability of the current pyridiniumaldoximes 2-PAM, obidoxime and HI-6.

The invention claimed is:

1. Compound chosen from:

compounds of formula (II) and their pharmaceutically acceptable salts:

(II)

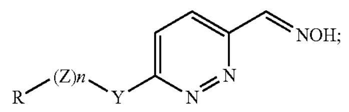

compounds of formula (III) and their pharmaceutically acceptable salts:

(III)

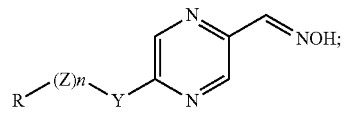

compounds of formula (IV) and their pharmaceutically acceptable salts:

(IV)

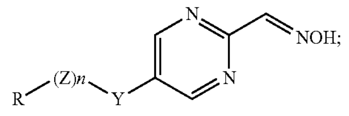

and compounds of formula (V) and their pharmaceutically acceptable salts:

(V)

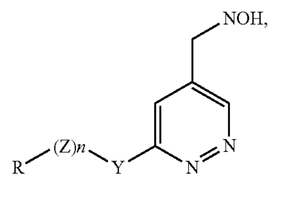

wherein:

Y is $-CH_2-CH_2-$, $-C\equiv C-$ or $-CH=CH-$;

Z is $-CH_2-$, n is an integer from 0 to 3; and

R is an alkyl group, a heteroalkyl, an aryl, a heteroaryl, a heterocycloalkyl, a biomolecule, a carboxyl group, a hydroxyl group, a cyano, an oxime, an hydroxamic group, a ketone, a thiol or thioether or thioester group, a phosphate, a phosphonate, phosphinate, phosphonium, sulfone, sulfonium, sulfate group, a fluorescent probe, or a group —N(R1)(R2), wherein R1 and R2 are each independently H, an alkyl group, an aryl or a heteroaryl.

2. Compound according to claim 1, which is a salt of a compound of any one of the formula (II) to (V) with an acid or a base.

3. Compound according to claim 1, wherein R is a heteroaryl.

4. Compound according to claim 1, wherein R is a heteroaryl which is not substituted, or alternatively a heteroaryl substituted by at least an alkyl group.

5. Compound according to claim 1, wherein it is chosen from:

compounds of formula (II) and their pharmaceutically acceptable salts, wherein:

Y is $—CH_2—CH_2—$ or —C≡C—, n is 0, 1 or 2; and

R is a heteroaryl;

compounds of formula (III) and their pharmaceutically acceptable salts, wherein:

Y is $—CH_2—CH_2—$, n is 0, 1 or 2; and

R is a heteroaryl;

compounds of formula (IV) and their pharmaceutically acceptable salts, wherein:

Y is $—CH_2—CH_2—$, n is 0, 1 or 2; and

R is a heteroaryl; and compounds of formula (V) and their pharmaceutically acceptable salts:

Y is $—CH_2—CH_2—$, n is 0, 1 or 2; and

R is a heteroaryl.

6. Compound according to claim 1, wherein it is chosen from:

compounds of formula (II) and their pharmaceutically acceptable salts, wherein:

Y is $—CH_2—CH_2—$ or —C≡C—, n is 0 or 2; and

R is a heteroaryl which is not substituted and is 2-, 3- or 4-pyridino, or is an imidazole which is substituted by at least an alkyl group;

compounds of formula (III) and their pharmaceutically acceptable salts, wherein:

Y is $—CH_2—CH_2—$, n is 0 or 2; and

R is a heteroaryl which is not substituted and is 2-, 3- or 4-pyridino;

compounds of formula (IV) and their pharmaceutically acceptable salts, wherein:

Y is $—CH_2—CH_2—$, n is 0 or 2; and

R is a heteroaryl which is not substituted and is 2-, 3- or 4-pyridino; and compounds of formula (V) and their pharmaceutically acceptable salts:

Y is $—CH_2—CH_2—$, n is 0; and

R is a heteroaryl which is not substituted and is 2-, 3- or 4-pyridino.

7. Compound according to claim 1, wherein it is chosen from:

(E)-6-(pyridin-3-ylethynyl)pyridazine-3-carbaldehyde oxime 4:

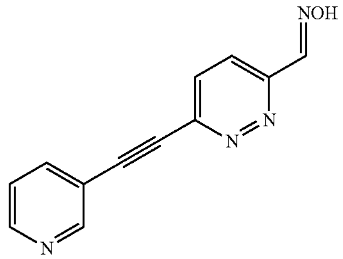

4

(E)-6-(pyridin-3-ylethynyl)pyridazine-3-carbaldehyde oxime hydrochloride NM-45:

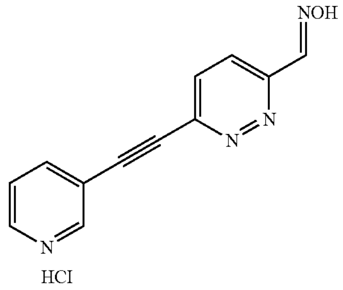

NM-45

(E)-6-(2-(pyridin-3-yl)ethyl)pyridazine-3-carbaldehyde oxime 5:

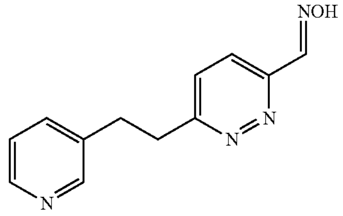

5

(E)-6-(2-(pyridin-3-yl)ethyl)pyridazine-3-carbaldehyde oxime hydrochloride NM-65:

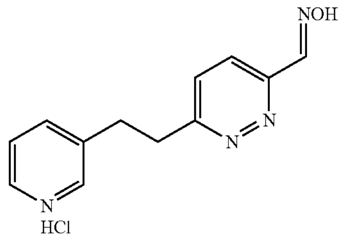

NM-65

(E/Z)-6-(4-(pyridin-3-yl)but-1-ynyl)pyridazine-3-carbaldehyde oxime 7:

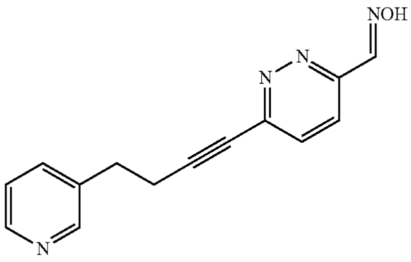

7

(E/Z)-6-(4-(pyridin-3-yl)but-1-ynyl)pyridazine-3-carbaldehyde oxime hydrochloride NM-184:

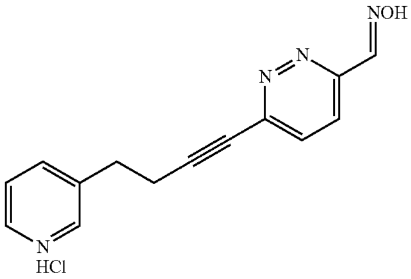

NM-184

(E/Z)-6-(4-(pyridin-3-yl)butyl)pyridazine-3-carbaldehyde oxime 8:

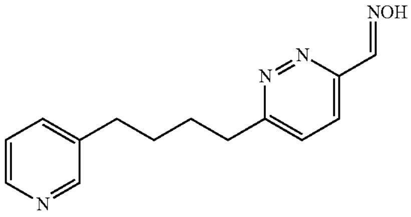

8

(E/Z)-6-(4-(pyridin-3-yl)butyl)pyridazine-3-carbaldehyde hydrogen chloride NM-201:

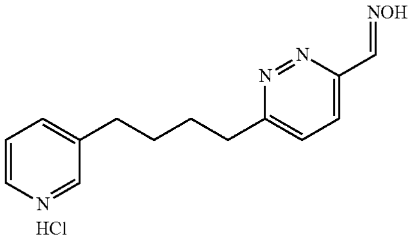

NM-201

(E)-5-(2-(pyridin-3-yl)ethyl)pyrazine-2-carbaldehyde oxime 13:

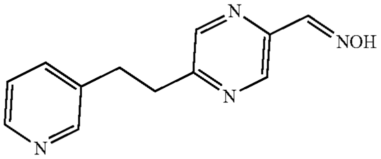

13

(E)-5-(2-(pyridin-3-yl)ethyl)pyrazine-2-carbaldehyde oxime hydrogen chloride NM-118:

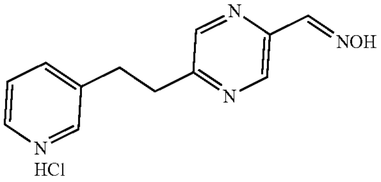

NM-118

5-(4-(pyridin-3-yl)butyl)pyrazine-2-carbaldehyde oxime 17:

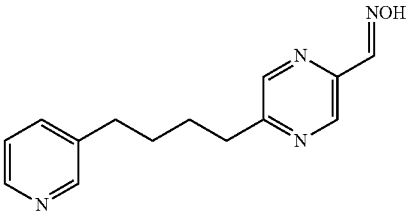

17

(E)-5-(4-(pyridin-3-yl)butyl)pyrazine-2-carbaldehyde oxime hydrochloride NM-202:

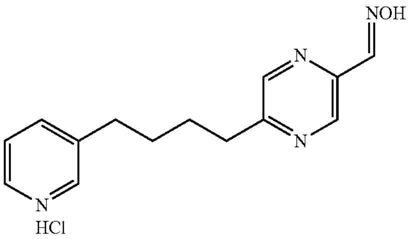

NM-202

(E)-5-(2-(pyridin-3-yl)ethyl)pyrimidine-2-carbaldehyde oxime 22:

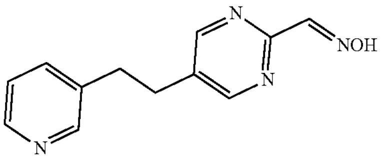

22

(E)-5-(2-(pyridin-3-yl)ethyl)pyrimidine-2-carbaldehyde oxime hydrochloride NM-158:

NM-158

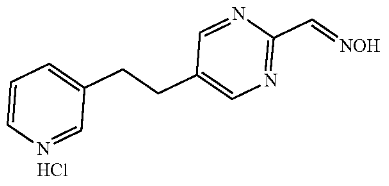

(E)-5-(4-(pyridin-3-yl)butyl)pyrimidine-2-carbaldehyde oxime:

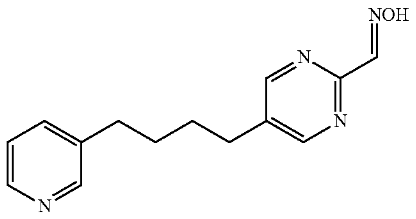

(E)-5-(4-(pyridin-3-yl)butyl)pyrimidine-2-carbaldehyde oxime hydrochloride NM-251:

NM-251

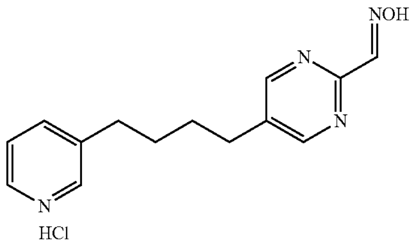

(E)-6-(2-(pyridin-3-yl)ethyl)pyridazine-4-carbaldehyde oxime:

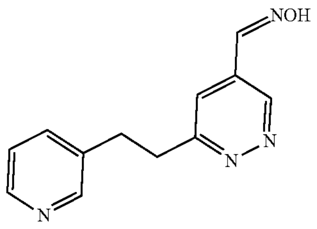

(E)-6-(2-(pyridin-3-yl)ethyl)pyridazine-4-carbaldehyde oxime hydrochloride NM-279:

NM-279

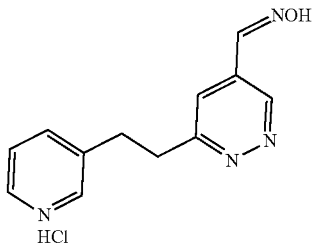

and (Z/E)-6-((1-methyl-1H-imidazol-5-yl) ethynyl) pyridazine-3-carbaldehyde oxime FR-156:

FR-156

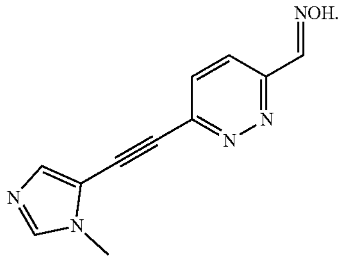

8. A pharmaceutical composition comprising at least one compound according to claim 1, and at least one pharmaceutically acceptable support.

9. The compound according to claim 2 wherein R is a heteroaryl.

10. The compound of claim 2 wherein the heteroaryl is a pyridine group.

11. The compound of claim 10 wherein the pyridine group is selected from 2-, 3- or 4-pyridino.

12. The compound of claim 9 wherein R is an imidazole.

13. The compound of claim 12 wherein the imidazole is substituted by at least one alkyl group.

14. The compound according to claim 2 wherein said salt is a chlorohydrate salt.

15. The compound according to claim 3 wherein the heteroaryl is a pyridine group.

16. The compound of claim 14 wherein the pyridine group is selected from 2-, 3- or 4-pyridino.

17. The compound of claim 3 wherein the heteroaryl is an imidazole.

18. The compound of claim 17 wherein the imidazole is substituted by at least one alkyl group.

* * * * *